US008765423B2

(12) United States Patent
Ochiai

(10) Patent No.: US 8,765,423 B2
(45) Date of Patent: Jul. 1, 2014

(54) DIACYLGLYCEROL ACYLTRANSFERASE GENES AND USE THEREOF

(75) Inventor: Misa Ochiai, Osaka (JP)

(73) Assignee: Suntory Holdings Limited, Osaka (JP)

( * ) Notice: Subject to any disclaimer, the term of this patent is extended or adjusted under 35 U.S.C. 154(b) by 0 days.

(21) Appl. No.: 13/512,109

(22) PCT Filed: Dec. 20, 2010

(86) PCT No.: PCT/JP2010/072930
§ 371 (c)(1),
(2), (4) Date: May 25, 2012

(87) PCT Pub. No.: WO2011/078134
PCT Pub. Date: Jun. 30, 2011

(65) Prior Publication Data
US 2012/0277451 A1 Nov. 1, 2012

(30) Foreign Application Priority Data

Dec. 21, 2009 (JP) ................................ 2009-289287

(51) Int. Cl.
*C12N 9/10* (2006.01)
*C12N 15/63* (2006.01)
*C07H 21/04* (2006.01)

(52) U.S. Cl.
USPC ..... 435/134; 536/23.2; 435/193; 435/254.11; 435/320.1

(58) Field of Classification Search
None
See application file for complete search history.

(56) References Cited

U.S. PATENT DOCUMENTS

| 6,822,141 | B2 | 11/2004 | Lardizabal et al. |
| 8,110,388 | B2 | 2/2012 | Ochiai et al. |
| 8,247,209 | B2 | 8/2012 | Ochiai et al. |
| 2006/0094086 | A1 | 5/2006 | Yadav et al. |
| 2006/0094087 | A1 | 5/2006 | Xue et al. |
| 2010/0323085 | A1 | 12/2010 | Ochiai |
| 2012/0115231 | A1 | 5/2012 | Ochiai |

FOREIGN PATENT DOCUMENTS

| EP | 1852114 | 11/2007 |
| JP | 2002-541783 | 12/2002 |
| RU | 2 272 073 | 8/2003 |
| WO | 00/60095 | 10/2000 |
| WO | 03/064444 | 8/2003 |
| WO | 2008/147562 | 12/2008 |

OTHER PUBLICATIONS

Sorger et al., "Synthesis of Triacylglycerols by the Acyl-Coenzyme A:Diacyl-Glycerol Acyltransferase Dga1p in Lipid Particles of the Yeast *Saccharomyces cerevisiae*", Journal of Bacteriology, vol. 184, No. 2, pp. 519-524 (2002).

Sandager et al., "Storage Lipid Synthesis Is Non-essential in Yeast", The Journal of Biological Chemistry, vol. 277, No. 8, pp. 6478-6482 (published Dec. 10, 2001).
Collected Abstract of the 2003 Annual Meeting of the Japan Society of Agricultureal and Biological Chemistry (2003).
Domergue et al., "Acyl Carriers Used as Substrates by the Desaturases and Elongases Involved in Very Long-chain Polyunsaturated Fatty Acids Biosynthesis Reconstituted in Yeast", The Journal of Biological Chemistry, vol. 278, No. 37, pp. 35115-35126 (2003).
Sorger et al., "Triacylglycerol biosynthesis in yeast", Appl. Microbiol. Biotechnol., vol. 61, No. 4, pp. 289-299 (2003).
Ochiai et al., "Mortierella alpine Yurai Diacylglycerol Acyl-ki Ten'I Koso Idenshi no Cloning to shokubutsu deno Hatsugen", Japan Society for Bioscience, Biotechnology, and Agrochemistry 2003 Nendo (Heisei 15 Nendo) Taikai Koen Yoshishu, Mar. 5, 2003, 2A07p. 19.
Kamisaka, "Cell Biological Studies on Intracellular Trafficking of Lipids. Biosynthesis of Triacylglycerol and Related Intracellular Lipid Transport in Filamentous Fungi and Yeast", Protein, nucleic acid and enzyme, vol. 44, No. 8, pp. 1207-1212 (1999).
Cases et al., "Identification of a gene encoding an acyl CoA:diacylglycerol acyltransferase, a key enzyme in triacylglycerol synthesis", Proc. Natl. Acad. Sci. USA, vol. 95, pp. 13018-13023 (1998).
Lardizabal et al., "DGAT2 Is a New Diacylglycerol Acyltransferase Gene Family", The Journal of Biological Chemistry, vol. 276, No. 42, pp. 38862-38869 (2001).
Oelkers et al., "A Lecithin Cholesterol Acyltransferase-like Gene Mediates Diacylglycerol Esterification in Yeast", The Journal of Biological Chemistry, vol. 275, No. 21, pp. 15609-15612 (2000).
Dahlqvist et al., "Phospholipid:diacylglycerol acyltrasferase: An enzyme that catalyzes the acyl-CoA-independent formation of triacylglycerol in yeast and plants", Proc. Natl. Acad. Sci. USA, vol. 97, No. 12, pp. 6487-6492 (2000).
Stahl et al., "Cloning and Functional Characterization of a Phospholipid: Diacylglycerol Acyltransferase from Arabidopsis", Plant Physiol., vol. 135, No. 3, pp. 1324-1335 (2004).
U.S. Appl. No. 13/575,700 to Misa Ochiai, filed Jul. 27, 2012.
U.S. Appl. No. 13/496,081 to Misa Ochiai, filed Mar. 14, 2012.
Search report from International Application No. PCT/JP2010/072930, mail date is Feb. 8, 2011.
International Preliminary Report on Patentability for International Application No. PCT/JP2010/072930, dated Jul. 10, 2012.
Database Geneseq, Jun. 29, 2006, XP-002696248.
"Transformation of Oil-Producing Fungus, *Mortierella alpine* 1S-4, Using Zeocin, and Application to Arachidonic Acid Production", Journal of Bioscience and Bioengineeing, vol. 100, No. 6, 617-622, 2005.
European Search Report in regard to European Appl. No. 10839364.6, dated Jun. 19, 2013.
Official Decision on Grant issued with respect to Russian Patent Application No. 2012131283, dated Dec. 11, 2013, along with an English language translation.

*Primary Examiner* — Kagnew H Gebreyesus
(74) *Attorney, Agent, or Firm* — Greenblum & Bernstein, P.L.C.

(57) ABSTRACT

It is an object to provide a novel diacylglycerol acyltransferase. The present invention relates to a diacylglycerol acyltransferase, a polynucleotide encoding the same, and so on. The present invention provides a polynucleotide comprising the nucleotide sequence of, e.g., SEQ ID NO: 1 or 4, a polynucleotide encoding a protein consisting of the amino acid sequence of SEQ ID NO: 2, an expression vector and transformant comprising the polynucleotide, a method for producing a lipid or fatty acid composition using the transformant, or a food, etc. comprising the lipid or fatty acid produced by the method.

13 Claims, 7 Drawing Sheets

```
         1601                                                                                    1700
genome   TCTAATCTGGAGCTTTCCCTCAAAGTCACAGGGGAGAAAAATGTCCTGGTTGCTCACTCCATGGGCTCGACGGTCCTGTTTTACTTTTTCAAATGGGTCG
cDNA     TCTAATCTGGAGCTTTCCCTCAAAGTCACAGGGGAGAAAAATGTCCTGGTTGCTCACTCCATGGGCTCCACGGTCCTGTTTTACTTTTTCAAATGGGTCG 1701                                                                                    1800
genome   AATCTGAGGAAGGCGGCAAGGGCGGACCCAACTGGGTGAACGACCACGTACATACATTCGTCAACATTGCGGGACCTATGCTAGGAGTACCCAAGACACT
cDNA     AATCTGAGGAAGGCGGCAAGGGCGGACCCAACTGGGTGAACGACCACGTACATACATTCGTCAACATTGCGGGACCTATGCTAGGAGTACCCAAGACACT 1801                                                                                    1900
genome   GGCTGCTGTACTTTCAGGAGAGGTACGGGATACTGCACAGCTGGGAGTCGTCAGCGGCATACGTTCTGGAAAAGTTCTTTTCGAGGCGGGAGCGGGCGGAC
cDNA     GGCTGCTGTACTTTCAGGAGAGGTACGGGATACTGCACAGCTGGGAGTCGTCAGCGGCATACGTTCTGGAAAAGTTCTTTTCGAGGCGGGAGCGGGCGGAC 1901                                                                                    2000
genome   CTGTTCAGGAGCTGGGGAGGACTGACAAGCATGATCGCCAAAGGAGGAAACCGTATCTGGGGAACGATTCATGGTGCACCGGATGATGGAACCCATGACG
cDNA     CTGTTCAGGAGCTGGGGAGGACTGACAAGCATGATCCCCAAAGGAGGAAACCGTATCTGGGGAACGATTCATGGTGCACCGGATGATGGAACCCATGACG 2001                                                                                    2100
genome   AGGAGGAAACTTTAGTGCAGGAGAAGATCTCAAAGAACCAGGAGGAACCCAATGCTACGACGAAGGGCAAGTGGGGCGACAAGGAATCACCGTCCTTTGG
cDNA     AGGAGGAAACTTTAGTGCAGGAGAAGATCTCAAAGAACCAGGAGGAACCCAATGCTACGACGAAGGGCAAGTGGGGCGACAAGGAATCACCGTCCTTTGG 2101                                                                                    2200
genome   AGCGATGCTGGCATTTGCAGAAGGTTCAGACATGGAGGCATCACACTATGGACGATAGGATGAAGCTGCTTTTTAAGACAGCTGGCGATGATTATAATGCT
cDNA     AGCGATGCTGGCATTTGCAGAAGGTTCAGACATGGAGGCATCACACTATGGACGATAGCATGAAGCTGCTTTTTTAAGACAGCTGGCGATGATTATAATGCT 2201                                                                                    2300
genome   ATGCTGGCTGACAATTACACTGTCGGCGCTTCAGTCACACAAGCGGAGATGGACAAGTCCGACAAACTGGGTACCAGCTGGTCCAACCCTCTGGAGGCGA
cDNA     ATGCTGGCTGACAATTACACTGTCGGCGCTTCAGTCACACAAGCGGAGATGGACAAGTCCGACAAACTGGGTACCAGCTGGTCCAACCCTCTGGAGGCGA 2301                                                                                    2400
genome   CGCTTCCTAAGGCGCCAAGATGAAGATTTACTGCCTGTACGGTGTCGGCAAGTCGACGGAGAGGAGCTATACGTACAACCGTATGATCGACCTCACACC
cDNA     CGCTTCCTAAGGCGCCAAGATGAAGATTTACTGCCTGTACGGTGTCGGCAAGTCGACGGAGAGGAGCTATACGTACAACCGTATGATCGACCTCACACC 2401                                                                                    2500
genome   ACAGATCTTTGACCAACGACCAGGAAATGTTTCGGACGAAACTGGCCAGGTCCCCAAGATTTACATGGACACGTCTGTTCACGACGAGAAGCTTGGTATC
cDNA     ACAGATCTTTGACCAACGACCAGGAAATGTTTCGGACGAAACTGGCCAGGTCCCCAAGATTTACATGGACACGTCTGTTCACGACGAGAAGCTTGGTATC 2501                                                                                    2600
genome   AGCTACGGTATCCATCAAGGCGACGGGTAATGCTCAATCGTCATTTGCTGCTACTTTGCTATTTTGTTGAACTTGATTGTTCGTTTCTAATTTTCGATCC
cDNA     AGCTACGGTATCCATCAAGGCGACGGG---------------------------------------------------------------------

2601                                                                                    2700
genome   TCTTGCCCATTTTACTGTAGAGATGGAACGGTCCCATTGCTTTCAACTGGATACATGTGTGTAGAAGGGTGGAACAAGAAGTTATATAATCGGGCCGGGA
cDNA     ------------------AGATGGAACGGTCCCATTGCTTTCAACTGGATACATGTGTGTAGAAGGGTGGAACAAGAAGTTATATAATCGGGCCGGGA 2701                                                                                    2800
genome   TCCAGATCATCACTCGTGAGTTTACGCACCAGAGCAGTCCCTCTCCGGTAGATATTCGTGGGGGCAAGAGGACGGGGGACCATGTCGACATGCTAGGCAA
cDNA     TCCAGATCATCACTCGTGAGTTTACGCACCAGAGCAGTCCCTCTCCGGTAGATATTCGTGGGGGCAAGAGGACGGGGGACCATGTCGACATGCTAGGCAA 2801                                                                                    2900
genome   CTACCAGGTGACGAAGGACCTGTTAACGATTGTAGCGGGACGGGATGGCGATGGTCTGGAAGAGCAGATATACTCGAAGATTCGTGAGTACTCTGCCAAG
cDNA     CTACCAGGTGACGAAGGACCTGTTAACGATTGTAGCGGGACGGGATGGCGATGGTCTGGAAGAGCAGATATACTCGAAGATTCGTGAGTACTCTGCCAAG 2901            2949
genome   GTCGACTTGTGATAATTTTTAGCTGTGCGCCATTAAAAAAAATTAGCCG
cDNA     GTCGACTTGTGATAATTTTTAGCTGTGCGCCATTAAAAAAAATTAGCCG
                         ***
```

Figure 2A

```
   1  ATGGCTTGGCGAGGGCAACTCACAATATCGTCGACCTTGAATATTTTCGGCTCAGCGAATTCACCAGCCGATATGATATCATTGATTTGT
      M  A  W  R  G  Q  L  T  I  S  S  T  L  N  I  F  G  S  A  N  S  P  A  D  M  I  S  L  I  C

91  ATATTTCAACGATTATTGATCCACTTTCCATTAGATCCACCTAACCGACAGACTTCATTCGAACATCCTTCAATGGCACCGAGAAAGAGG
      I  F  Q  R  L  L  I  H  F  P  L  D  P  P  N  R  Q  T  S  F  E  H  P  S  M  A  P  R  K  R

181  AAGCAGGCCAGTAGAAATAGGAGCAGCAGCAACTCCAGCACAAATCCCACCACCAATACTCAAATCAGCAGCGATGCACATAACGCACAG
      K  Q  A  S  R  N  R  S  S  S  N  S  S  T  N  P  T  T  N  T  Q  I  S  S  D  A  H  N  A  Q

271  GACACCCATGACGCTCTCAACACACATGCCAACGGAAAGGGCCCCATGAGCCAAGTTGAGCCAGAACCCCACTGCAGCACCAAAGAAGAG
      D  T  H  D  A  L  N  T  H  A  N  G  K  G  P  M  S  Q  V  E  P  E  P  H  C  S  T  K  E  E

361  ATCAAGGATGCCATCGCCAAGCTGTCCAACTCATTACCCAAAGATACCAAGATCGAGGTCAGGCACCCCTCTCTCAGTCGCAACCCCTCT
      I  K  D  A  I  A  K  L  S  N  S  L  P  K  D  T  K  I  E  V  R  H  P  S  L  S  R  N  P  S

451  GTCGGCGATTATCTGCATAAGGCGCTGTTCGTGAGTGAGGCCGAGGCCAAGAGCCGGAAAAAACACGTCGCCCCTGCCACCCGCCGTCGC
      V  G  D  Y  L  H  K  A  L  F  V  S  E  A  E  A  K  S  R  K  K  H  V  A  P  A  T  R  R  R

541  GTCATCCTTCTGCTTGGTATCATCATTGGCATGGGTCTGGCCACAGTCTTGATGCGGCAGTCCAAGGACGCAGCCTACATAGAAGCCTTC
      V  I  L  L  L  G  I  I  I  G  M  G  L  A  T  V  L  M  R  Q  S  K  D  A  A  Y  I  E  A  F

631  TCCCACTACTTTCAGGACTTTGACCTAGCCTCCATGGTCCCCTCTGGCATGATCCCAGACGAGTTCATTGGGAATGTATCAGCTATGTTC
      S  H  Y  F  Q  D  F  D  L  A  S  M  V  P  S  G  M  I  P  D  E  F  I  G  N  V  S  A  M  F

721  AAGCCAGAGATTCTGACCGAGGAAGAGTTCTATCCAGGAGAGGCACTGCGATCGGAGCAAGGTTATAGACCTAAGCACCCTGTTACCATG
      K  P  E  I  L  T  E  E  E  F  Y  P  G  E  A  L  R  S  E  Q  G  Y  R  P  K  H  P  V  T  M

811  ATTCCTGGAATCGTATCAACTGGCCTTGAGTCTTGGTCAACAACACACAACTGCTCCCAGAAATACTTCCGGAAGCGCATGTGGGGAACC
      I  P  G  I  V  S  T  G  L  E  S  W  S  T  T  H  N  C  S  Q  K  Y  F  R  K  R  M  W  G  T

901  ACAACCATGTTCAAAGCCGTGTTATTGGACAAAGACTGCTGGATCACTAATATGCGACTCGATCCAAAGACAGGACTAGACCCGGAGGGG
      T  T  M  F  K  A  V  L  L  D  K  D  C  W  I  T  N  M  R  L  D  P  K  T  G  L  D  P  E  G

991  GTTCGATTACGCGCCGCTCAGGGATTGGAAGCTGCCGACTACTTTGTTCAGGGGTATTGGGTATGGGCGCCCATTATCAAGAACTTGGCA
      V  R  L  R  A  A  Q  G  L  E  A  A  D  Y  F  V  Q  G  Y  W  V  W  A  P  I  I  K  N  L  A

1081  GCCATCGGATACGACAACAACAATATGCATCTCGCATCCTATGACTGGAGGTTATCGTTTGCCAATCTGGAGAACAGAGACAAGTACTTT
      A  I  G  Y  D  N  N  N  M  H  L  A  S  Y  D  W  R  L  S  F  A  N  L  E  N  R  D  K  Y  F

1171  TCCCGACTGAAGTCTAATCTGGAGCTTTCCCTCAAAGTCACAGGGGAGAAAAATGTCCTGGTTGCTCACTCCATGGGCTCCACGGTCCTG
      S  R  L  K  S  N  L  E  L  S  L  K  V  T  G  E  K  N  V  L  V  A  H  S  M  G  S  T  V  L

1261  TTTTACTTTTTCAAATGGGTCGAATCTGAGGAAGGCGGCAAGGGCGGACCCAACTGGGTGAACGACCACGTACATACATTCGTCAACATT
      F  Y  F  F  K  W  V  E  S  E  E  G  G  K  G  G  P  N  W  V  N  D  H  V  H  T  F  V  N  I

1351  GCGGGACCTATGCTAGGAGTACCCAAGACACTGGCTGCTGTACTTTCAGGAGAGGTACGGGATACTGCACAGCTGGGAGTCGTCAGCGCA
      A  G  P  M  L  G  V  P  K  T  L  A  A  V  L  S  G  E  V  R  D  T  A  Q  L  G  V  V  S  A

1441  TACGTTCTGGAAAAGTTCTTTTCGAGGCGGAGCGGGCGGACCTGTTCAGGAGCTGGGGAGGACTGACAAGCATGATCCCCAAAGGAGGA
      Y  V  L  E  K  F  F  S  R  R  E  R  A  D  L  F  R  S  W  G  G  L  T  S  M  I  P  K  G  G

1531  AACCGTATCTGGGGAACGATTCATGGTGCACCGGATGATGGAACCCATGACGAGGAGGAAACTTTAGTGCAGGAGAAGATCTCAAAGAAC
      N  R  I  W  G  T  I  H  G  A  P  D  D  G  T  H  D  E  E  E  T  L  V  Q  E  K  I  S  K  N

1621  CAGGAGGAACCCAATGCTACGACGAAGGGCAAGTGGGGCGACAAGGAATCACCGTCCTTTGGAGCGATGCTGGCATTTGCAGAAGGTTCA
      Q  E  E  P  N  A  T  T  K  G  K  W  G  D  K  E  S  P  S  F  G  A  M  L  A  F  A  E  G  S

1711  GACATGGAGCATCACACTATGGACGATAGCATGAAGCTGCTTTTTAAGACAGCTGGCGATGATTATAATGCTATGCTGGCTGACAATTAC
      D  M  E  H  H  T  M  D  D  S  M  K  L  L  F  K  T  A  G  D  D  Y  N  A  M  L  A  D  N  Y

1801  ACTGTCGGCGCTTCAGTCACACAAGCGGAGATGGACAAGTCCGACAAACTGGCTACCAGCTGGTCCAACCCTCTGGAGGCGACGCTTCCT
      T  V  G  A  S  V  T  Q  A  E  M  D  K  S  D  K  L  A  T  S  W  S  N  P  L  E  A  T  L  P
```

Figure 2B

```
1891  AAGGCGCCCAAGATGAAGATTTACTGCCTGTACGGTGTCGGCAAGTCGACCGAGAGGAGCTATACGTACAACCGTATGATCGACCTCACA
       K  A  P  K  M  K  I  Y  C  L  Y  G  V  G  K  S  T  E  R  S  Y  T  Y  N  R  M  I  D  L  T

1981  CCACAGATCTTTGACCAACGACCAGGAAATGTTTCGGACGAAACTGGCCAGGTCCCCAAGATTTACATCGACACGTCTGTTCACGACGAG
       P  Q  I  F  D  Q  R  P  G  N  V  S  D  E  T  G  Q  V  P  K  I  Y  I  D  T  S  V  H  D  E

2071  AAGCTTGGTATCAGCTACGGTATCCATCAAGGCGACGGAGATGGAACGGTCCCATTGCTTTCAACTGGATACATGTGTGTAGAAGGGTGG
       K  L  G  I  S  Y  G  I  H  Q  G  D  G  D  G  T  V  P  L  L  S  T  G  Y  M  C  V  E  G  W

2161  AACAAGAAGTTATATAATCCGGGCGGGATCCAGATCATCACTCGTGAGTTTACGCACCAGAGCAGTCCCTCTCCGGTAGATATTCGTGGG
       N  K  K  L  Y  N  P  A  G  I  Q  I  I  T  R  E  F  T  H  Q  S  S  P  S  P  V  D  I  R  G

2251  GGCAAGAGGACGGCGGACCATGTCGACATCCTAGGCAACTACCAGGTGACGAAGGACCTGTTAACGATTGTAGCGGGACGGGATGGCGAT
       G  K  R  T  A  D  H  V  D  I  L  G  N  Y  Q  V  T  K  D  L  L  T  I  V  A  G  R  D  G  D

2341  GGTCTGGAAGAGCAGATATACTCGAAGATTCGTGAGTACTCTGCCAAGGTCGACTTGTGATAATTTTTAGCTGTGCGCCATTAAAAAAAA
       G  L  E  E  Q  I  Y  S  K  I  R  E  Y  S  A  K  V  D  L

2431  TTAGCCGAAAAAAAAAAAAAAAAAAAAAA
```

Figure 3

|  | 1 | 100 |
|--|---|-----|
| M. alpina | MAWRGGLTISSTLNIFGSANSPADMISLICIFQRLLIHFPLQPPNRQTSFEHPSMAPRKRKQASRNRSSSNSSTNPTTNTQISSDAHNAQDTHDALNTHA | |
| U. maydis | ----------------------------------MNNRKHKRNGASHQSNENATSSAHQLNRYSN-IASSSTASNSNDGATTPPQQIVLNKSKRPSMKGRA | |
| Y. lipolytica | -------------------------------------------MTQPVNRKAT-VERVEPAVEVADSESEAKTDVHVHHHHHHKRKSV | |
| S. cerevisiae | -------------------------------------------MGTLFRRNVQ-NQKSDSDENNKGGSVHNKRESRNHIHHQQGLGHKR | |

|  | 101 | 200 |
|--|-----|-----|
| M. alpina | NGKGPMSQVEPEPHCSTKEEIKDAIAKLSNSLPKDTKIEVRHPSLSRNPSVGDYLHKALFVSEAEAKSRKKHVAPATRRRVILLLGIIIGMGLATVLMRQ | |
| U. maydis | --SYSVTAPGTPWHELDLSEIPFLRHDVADVPIKRGINRYRRLFFIFGATLGAVIAFLASRNVQMAQH----------------------VASLR | |
| Y. lipolytica | --KGKILNFFT-----RSRRITFVLGAVVGVIAAGYYAAPPELSIDIDALLGDLPSFDFDALSLDN---------------------------- | |
| S. cerevisiae | --RRGISGSAK-----RNERGKDFDRKRDGNGRK-RWRDSRRLIFILGAFLGVLLPESFGAYHVHNSD------------------SDLF- | |

|  | 201 | 300 |
|--|-----|-----|
| M. alpina | SKDAAYIEAFSHYFQDFDLASMVPSGMIPDEFIGNVSAMFKPEILTEEEFYPGEALRSEQGYRPKHPVTMIPGIVSTGLESWS----TTHNCSQKYFRKRM | |
| U. maydis | ALVDESIDGLGIDFPSIDIGMPKEFADMGDNLFSRSRE------WFKNKDFGVGROLSSEG-YSADHPVILIPGIVSTGLESW----TTDARSASYFRKRL | |
| Y. lipolytica | ----LSMDSVSDFVQDMKSRFPTKILQEAAKIEKHQKS-----EQKAAPFAVGKAMKSEG-LNAKYPVVLVPGVISTGLESHSLEGTEEGPTESHFRKRM | |
| S. cerevisiae | -DNFVNFDSLKVYLDDWKDVLPQGISSFIDDIQAGNYSTSS-LDDLSENFAVGKQLLRDYNIEAKHPVVMVPGVISTGIESWGVIGDDECDSSAHFRKRL | |

|  | 301 | 400 |
|--|-----|-----|
| M. alpina | WGTTTMFKAVLLDKDCNITNMRLDPKTGLDPEGVRLRAAQGLEAADYFVQGYWVHAPIIKNLAAIGYDNNMHHLASYDWRLSFANLENRDKYFSRLKSNL | |
| U. maydis | WGTTTMMRTIVFEKEMWVRHLSLDPETGLDPCGIRVRAAEGLDAASFEAAGYWIWSKVIENLAVLGYDTNNLFLASYDWRLSFYNLEVRDRYFTRLKLKI | |
| Y. lipolytica | WGSWYMIRVWLLDKYCNLQNLMLDTETGLDPPHFKLRAAQGFASADFFMAGYWLMNKLLENLAVIGYDTDTNSAAAYDWRLSYPDLEHRDGYFSKLKASI | |
| S. cerevisiae | WGSFYMLRTMVMDKVGNLKHVWLDPETGLDPPNFTLRAAQGFESTDYFIAGYWIWNKVFDNLGVIGYFPNKMTSAAYDWRLAYLDLERRDRYFTKLKEQI | |

|  | 401 | 500 |
|--|-----|-----|
| M. alpina | ELSLKVTGEKNVLVAHSMGSTVLFYFFKWVESEEG--GKGGPMWVNDHVHTFVNIAGPMLGVPKTLAAVLSGEVRDIAQLGVVSAYVLEKFFSRRERADL | |
| U. maydis | EQNKALFGKKTVIVAHSMGSSVFYYFMKWVEAEGDFYGNGGPMWVEDHIEAFTSIAGTFLGVPKAMAVMLSGEMRDTVEVPPAAAYLLEKFFSRRERAKL | |
| Y. lipolytica | EETKRMTGEKTVLTGHSMGSQVIFYFMKWAEAEG---YGGGGPMWVNDHIESFVDISGSMLGTPKTLVALLSGENKDTVQLNAMAVYGLEQFFSRRERADL | |
| S. cerevisiae | ELFHQLSGEKVCLIGHSMGSQIIFYFMKWVEAEGPLYGNGGRGMVNEHIDSFINAAGTLLGAPKAVPALISGENKDTIQLNTLAMYGLEKFFSRIERVKM | |
|  | * | |

|  | 501 | 600 |
|--|-----|-----|
| M. alpina | FRSWGGLTSMIPKGGNRLWGTIHGAPDDGTHDEEETLVQEKISKNQEEPNATTKGKWGDKESPSFGAMLAFAEGSDMEHHTMDDSMKLLFKTAGDDYNAM | |
| U. maydis | FRTWAGGASMLIKGGEDIWGNSTWAPDDEQDAE-DTHGHIYSFR---QPSAQQHNLNEH-----------TVRINLTATEAHNFMLQHAPSSFQKM | |
| Y. lipolytica | LRTWGGIASMIPKGGKALWGDHSGAPDDEPGQN-VTFGNFIKFK----ESLTEYSAK-----------------NLTMDETVDFLYSQSPEWFVNR | |
| S. cerevisiae | LQTWGGIPSMLPKGEEVIWGDMKSSSEDALNNNTDIYGNFIRFE---RNTSDAFNK-----------------NLTMKDAINMTLSISPEWLQRR | |

|  | 601 | 700 |
|--|-----|-----|
| M. alpina | LADNYTVGASVTQAEMDKSDKLATSNSNPLEATLFKAPKNMKLYCLYGVGKSTERSYTYNRMIDLTPQIFDQRPGNVSDETGQVPKIYIDTSVHDEKLG-- | |
| U. maydis | LATNYSHGIERDPAKLEANNADHTKNSNPLEAPLPNAPSMKLYCIYGVGKPTERSYWYQQGEFVTESSIGEQMDEPGCFGEECPDVSRTPALNFPTARLS | |
| Y. lipolytica | TEGAYSFGIAKTRKQVEQNEKRPSTWSNPLEAALPNAPDLKIYCFYGVGKDTERAYYYGDE---------PNPEQTNLNVSIAGNDPDG------- | |
| S. cerevisiae | VHEQYSFGYSKNEEELRKNELHHKHWSNPMEVPLPEAPHMKIYCIYGVNNPTERAYVYKEE---------DDSSALNLTIDYESKQP--------- | |

|  | 701 | 800 |
|--|-----|-----|
| M. alpina | -----------ISYGIHQGDGDGTVPLLSTGYMCVEGWNKKLYNPAGIQIITREFTHQSSPSPVDIRGGKRTADHVDILGNYQVTKDLLTIVAGRDG | |
| U. maydis | WIDHVIQKEDAVPKVRAGCKWGEGDGTVSLLSLGAMCTOGWKHSIWNPANISVVFHELKHE--PEAMDLRGGESTGDHVDILGARGVNEAILKIAAG-RG | |
| Y. lipolytica | -----------YLWEGOGDGTVSLVTHTMCHRNKDENSKFNPGNAQVKVVEWLHQ--PDRLDIRGGAQTAEHVDILGRSELNEMVLKVASG-KG | |
| S. cerevisiae | -----------VFLTEGDGTVPLVAHSMCHKNAQGASPYNPAGINVTIVEMKHQ--PDRFDIRGGAKSAEHVDILGSAELNDYILKIASG-NG | |
|  | * | * |

|  | 801 | 827 |
|--|-----|-----|
| M. alpina | DGLEEQIYSKIREYSAKVDL------- | |
| U. maydis | QEVGDQFFSDIRQYASNVKWLGDEPGP | |
| Y. lipolytica | NEIEERVISNIDEWVWKIDLGSN---- | |
| S. cerevisiae | DLVEPRQLSNLSQWVSQMPFPM----- | |

Alignment comparison of the amino acid sequences of PDAT homologues of fungi origin.
* Amino acid residues of putative active center Figure 4
Fatty Acid Content (μg) in the Lipid Fraction Extracted from Yeast Cells (10 ml of the culture)
A : PL、 B : TG
A
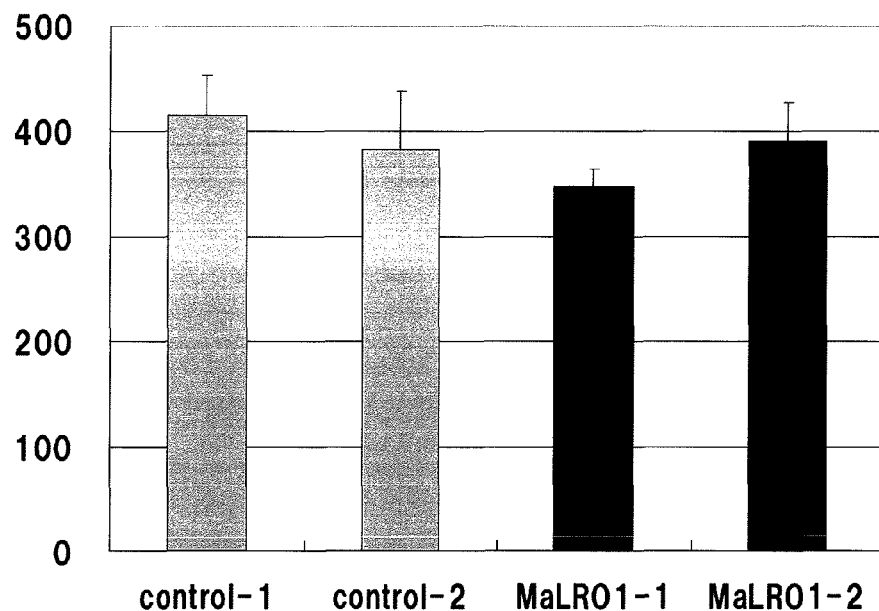
B
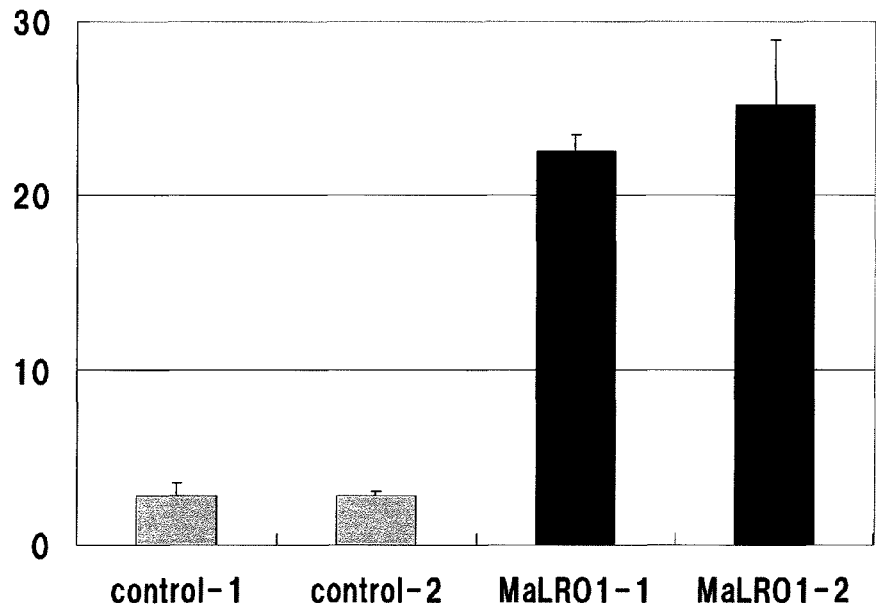

Figure 5
A. Fatty Acid Composition of TG
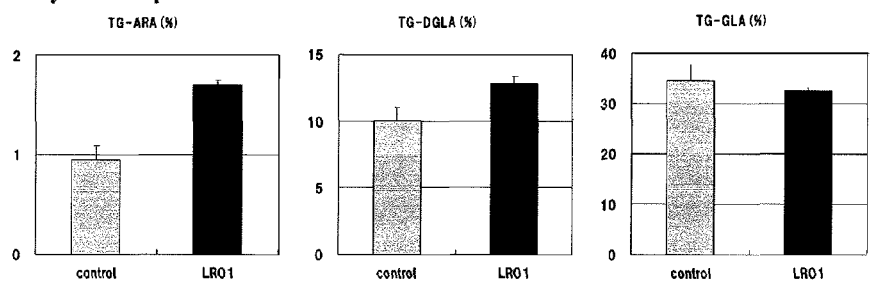
B. Fatty Acid Composition of PL
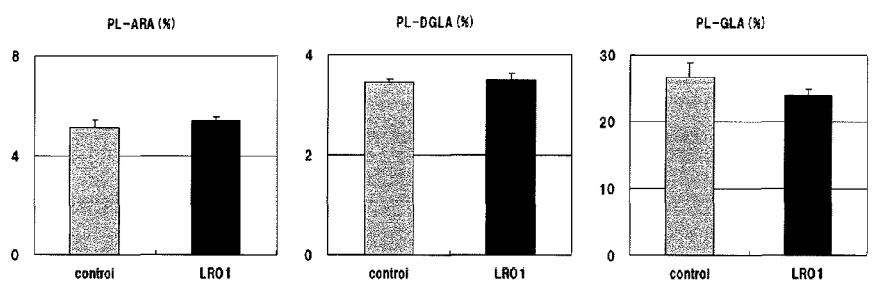

SEQUENCE LISTING

```
<160> NUMBER OF SEQ ID NOS: 27

<210> SEQ ID NO 1
<211> LENGTH: 2397
<212> TYPE: DNA
<213> ORGANISM: Mortierella alpina

<400> SEQUENCE: 1
atggcttggc gagggcaact cacaatatcg tcgaccttga atattttcgg ctcagcgaat      60
tcaccagccg atatgatatc attgatttgt atatttcaac gattattgat ccactttcca     120
ttagatccac ctaaccgaca gacttcattc gaacatcctt caatggcacc gagaaagagg     180
aagcaggcca gtagaaatag gagcagcagc aactccagca caaatcccac caccaatact     240
caaatcagca gcgatgcaca taacgcacag gacacccatg acgctctcaa cacacatgcc     300
aacggaaagg gccccatgag ccaagttgag ccagaacccc actgcagcac caaagaagag     360
atcaaggatg ccatcgccaa gctgtccaac tcattaccca aagataccaa gatcgaggtc     420
aggcacccct ctctcagtcg caaccccttct gtcggcgatt atctgcataa ggcgctgttc     480
gtgagtgagg ccgaggccaa gagccggaaa aaacacgtcg cccctgccac ccgccgtcgc     540
gtcatccttc tgcttggtat catcattggc atgggtctgg ccacagtctt gatgcggcag     600
tccaaggacg cagcctacat agaagcctttc tcccactact ttcaggactt tgacctagcc     660
tccatggtcc cctctggcat gatcccagac gagttcattg ggaatgtatc agctatgttc     720
aagccagaga ttctgaccga ggaagagttc tatccaggag aggcactgcg atcggagcaa     780
ggttatagac ctaagcaccc tgttaccatg attcctggaa tcgtatcaac tggccttgag     840
```

```
tcttggtcaa caacacacaa ctgctcccag aaatacttcc ggaagcgcat gtggggaacc    900
acaaccatgt tcaaagccgt gttattggac aaagactgct ggatcactaa tatgcgactc    960
gatccaaaga caggactaga cccggagggg gttcgattac gcgccgctca gggattggaa   1020
gctgccgact actttgttca ggggtattgg gtatgggcgc ccattatcaa gaacttggca   1080
gccatcggat acgacaacaa caatatgcat ctcgcatcct atgactggag gttatcgttt   1140
gccaatctgg agaacagaga caagtacttt tcccgactga agtctaatct ggagcttttcc  1200
ctcaaagtca caggggagaa aaatgtcctg gttgctcact ccatgggctc cacggtcctg   1260
ttttactttt tcaaatgggt cgaatctgag gaaggcggca agggcggacc caactgggtg   1320
aacgaccacg tacatacatt cgtcaacatt gcgggaccta tgctaggagt acccaagaca   1380
ctggctgctg tactttcagg agaggtacgg gatactgcac agctgggagt cgtcagcgca   1440
tacgttctgg aaaagttctt ttcgaggcgg gagcgggcgg acctgttcag gagctgggga   1500
ggactgacaa gcatgatccc caaggagga accgtatct ggggaacgat tcatggtgca    1560
ccggatgatg gaacccatga cgaggaggaa actttagtgc aggagaagat ctcaaagaac   1620
caggaggaac ccaatgctac gacgaagggc aagtggggcg acaaggaatc accgtccttt   1680
ggagcgatgc tggcatttgc agaaggttca gacatggagc atcacactat ggacgatagc   1740
atgaagctgc ttttaagac agctggcgat gattataatg ctatgctggc tgacaattac    1800
actgtcggcg cttcagtcac acaagcggag atggacaagt ccgacaaact ggctaccagc   1860
tggtccaacc ctctggaggc gacgcttcct aaggcgccca agatgaagat ttactgcctg   1920
tacggtgtcg gcaagtcgac cgagaggagc tatacgtaca accgtatgat cgacctcaca   1980
ccacagatct ttgaccaacg accaggaaat gttttcggacg aaactggcca ggtccccaag   2040
atttacatcg acacgtctgt tcacgacgag aagcttggta tcagctacgg tatccatcaa   2100
ggcgacggag atggaacggt cccattgctt tcaactggat acatgtgtgt agaagggtgg   2160
aacaagaagt tatataatcc ggccgggatc cagatcatca ctcgtgagtt tacgcaccag   2220
agcagtccct ctccggtaga tattcgtggg ggcaagagga cggcggacca tgtcgacatc   2280
ctaggcaact accaggtgac gaaggacctg ttaacgattg tagcgggacg ggatggcgat   2340
ggtctggaag agcagatata ctcgaagatt cgtgagtact ctgccaaggt cgacttg     2397
```

<210> SEQ ID NO 2
<211> LENGTH: 799
<212> TYPE: PRT
<213> ORGANISM: Mortierella alpina

<400> SEQUENCE: 2

```
Met Ala Trp Arg Gly Gln Leu Thr Ile Ser Ser Thr Leu Asn Ile Phe
1               5                   10                  15

Gly Ser Ala Asn Ser Pro Ala Asp Met Ile Ser Leu Ile Cys Ile Phe
                20                  25                  30

Gln Arg Leu Leu Ile His Phe Pro Leu Asp Pro Asn Arg Gln Thr
            35                  40                  45

Ser Phe Glu His Pro Ser Met Ala Pro Arg Lys Arg Lys Gln Ala Ser
    50                  55                  60

Arg Asn Arg Ser Ser Ser Asn Ser Ser Thr Asn Pro Thr Thr Asn Thr
65                  70                  75                  80

Gln Ile Ser Ser Asp Ala His Asn Ala Gln Asp Thr His Asp Ala Leu
                85                  90                  95

Asn Thr His Ala Asn Gly Lys Gly Pro Met Ser Gln Val Glu Pro Glu
```

```
            100                 105                 110
Pro His Cys Ser Thr Lys Glu Glu Ile Lys Asp Ala Ile Ala Lys Leu
        115                 120                 125

Ser Asn Ser Leu Pro Lys Asp Thr Lys Ile Glu Val Arg His Pro Ser
130                 135                 140

Leu Ser Arg Asn Pro Ser Val Gly Asp Tyr Leu His Lys Ala Leu Phe
145                 150                 155                 160

Val Ser Glu Ala Glu Ala Lys Ser Arg Lys Lys His Val Ala Pro Ala
                165                 170                 175

Thr Arg Arg Arg Val Ile Leu Leu Gly Ile Ile Gly Met Gly
        180                 185                 190

Leu Ala Thr Val Leu Met Arg Gln Ser Lys Asp Ala Ala Tyr Ile Glu
        195                 200                 205

Ala Phe Ser His Tyr Phe Gln Asp Phe Asp Leu Ala Ser Met Val Pro
        210                 215                 220

Ser Gly Met Ile Pro Asp Glu Phe Ile Gly Asn Val Ser Ala Met Phe
225                 230                 235                 240

Lys Pro Glu Ile Leu Thr Glu Glu Phe Tyr Pro Gly Glu Ala Leu
                245                 250                 255

Arg Ser Glu Gln Gly Tyr Arg Pro Lys His Pro Val Thr Met Ile Pro
                260                 265                 270

Gly Ile Val Ser Thr Gly Leu Glu Ser Trp Ser Thr Thr His Asn Cys
                275                 280                 285

Ser Gln Lys Tyr Phe Arg Lys Arg Met Trp Gly Thr Thr Thr Met Phe
        290                 295                 300

Lys Ala Val Leu Leu Asp Lys Asp Cys Trp Ile Thr Asn Met Arg Leu
305                 310                 315                 320

Asp Pro Lys Thr Gly Leu Asp Pro Glu Gly Val Arg Leu Arg Ala Ala
                325                 330                 335

Gln Gly Leu Glu Ala Ala Asp Tyr Phe Val Gln Gly Tyr Trp Val Trp
        340                 345                 350

Ala Pro Ile Ile Lys Asn Leu Ala Ala Ile Gly Tyr Asp Asn Asn Asn
        355                 360                 365

Met His Leu Ala Ser Tyr Asp Trp Arg Leu Ser Phe Ala Asn Leu Glu
        370                 375                 380

Asn Arg Asp Lys Tyr Phe Ser Arg Leu Lys Ser Asn Leu Glu Leu Ser
385                 390                 395                 400

Leu Lys Val Thr Gly Glu Lys Asn Val Leu Val Ala His Ser Met Gly
                405                 410                 415

Ser Thr Val Leu Phe Tyr Phe Phe Lys Trp Val Glu Ser Glu Glu Gly
                420                 425                 430

Gly Lys Gly Gly Pro Asn Trp Val Asn Asp His Val His Thr Phe Val
                435                 440                 445

Asn Ile Ala Gly Pro Met Leu Gly Val Pro Lys Thr Leu Ala Ala Val
                450                 455                 460

Leu Ser Gly Glu Val Arg Asp Thr Ala Gln Leu Gly Val Val Ser Ala
465                 470                 475                 480

Tyr Val Leu Glu Lys Phe Phe Ser Arg Arg Glu Arg Ala Asp Leu Phe
                485                 490                 495

Arg Ser Trp Gly Gly Leu Thr Ser Met Ile Pro Lys Gly Gly Asn Arg
                500                 505                 510

Ile Trp Gly Thr Ile His Gly Ala Pro Asp Asp Gly Thr His Asp Glu
                515                 520                 525
```

```
Glu Thr Leu Val Gln Glu Lys Ile Ser Lys Asn Gln Glu Glu Pro
    530                 535                 540

Asn Ala Thr Thr Lys Gly Lys Trp Gly Asp Lys Ser Pro Ser Phe
545                 550                 555                 560

Gly Ala Met Leu Ala Phe Ala Glu Gly Ser Asp Met Glu His His Thr
                565                 570                 575

Met Asp Asp Ser Met Lys Leu Leu Phe Lys Thr Ala Gly Asp Asp Tyr
            580                 585                 590

Asn Ala Met Leu Ala Asp Asn Tyr Thr Val Gly Ala Ser Val Thr Gln
        595                 600                 605

Ala Glu Met Asp Lys Ser Asp Lys Leu Ala Thr Ser Trp Ser Asn Pro
    610                 615                 620

Leu Glu Ala Thr Leu Pro Lys Ala Pro Lys Met Lys Ile Tyr Cys Leu
625                 630                 635                 640

Tyr Gly Val Gly Lys Ser Thr Glu Arg Ser Tyr Thr Tyr Asn Arg Met
                645                 650                 655

Ile Asp Leu Thr Pro Gln Ile Phe Asp Gln Arg Pro Gly Asn Val Ser
            660                 665                 670

Asp Glu Thr Gly Gln Val Pro Lys Ile Tyr Ile Asp Thr Ser Val His
        675                 680                 685

Asp Glu Lys Leu Gly Ile Ser Tyr Gly Ile His Gln Gly Asp Gly Asp
    690                 695                 700

Gly Thr Val Pro Leu Leu Ser Thr Gly Tyr Met Cys Val Glu Gly Trp
705                 710                 715                 720

Asn Lys Lys Leu Tyr Asn Pro Ala Gly Ile Gln Ile Ile Thr Arg Glu
                725                 730                 735

Phe Thr His Gln Ser Ser Pro Ser Pro Val Asp Ile Arg Gly Gly Lys
            740                 745                 750

Arg Thr Ala Asp His Val Asp Ile Leu Gly Asn Tyr Gln Val Thr Lys
        755                 760                 765

Asp Leu Leu Thr Ile Val Ala Gly Arg Asp Gly Asp Gly Leu Glu Glu
    770                 775                 780

Gln Ile Tyr Ser Lys Ile Arg Glu Tyr Ser Ala Lys Val Asp Leu
785                 790                 795

<210> SEQ ID NO 3
<211> LENGTH: 2400
<212> TYPE: DNA
<213> ORGANISM: Mortierella alpina

<400> SEQUENCE: 3
atggcttggc gagggcaact cacaatatcg tcgaccttga atattttcgg ctcagcgaat    60
tcaccagccg atatgatatc attgatttgt atatttcaac gattattgat ccactttcca   120
ttagatccac ctaaccgaca gacttcattc gaacatcctt caatggcacc gagaaagagg   180
aagcaggcca gtagaaatag gagcagcagc aactccagca caaatcccac caccaatact   240
caaatcagca gcgatgcaca taacgcacag gacacccatg acgctctcaa cacacatgcc   300
aacggaaagg gccccatgag ccaagttgag ccagaacccc actgcagcac caaagaagag   360
atcaaggatg ccatcgccaa gctgtccaac tcattaccca agataccaa gatcgaggtc    420 aggcacccct ctctcagtcg caaccectct gtcggcgatt atctgcataa ggcgctgttc   480
gtgagtgagg ccgaggccaa gagccggaaa aacacgtcg cccctgccac cgccgtcgc    540 gtcatccttc tgcttggtat catcattggc atgggtctgg ccacagtctt gatgcggcag   600
```

```
tccaaggacg cagcctacat agaagccttc tcccactact ttcaggactt tgacctagcc    660
tccatggtcc cctctggcat gatcccagac gagttcattg gaatgtatc agctatgttc     720 aagccagaga ttctgaccga ggaagagttc tatccaggag aggcactgcg atcggagcaa    780
ggttatagac ctaagcaccc tgttaccatg attcctggaa tcgtatcaac tggccttgag    840
tcttggtcaa caacacacaa ctgctcccag aaatacttcc ggaagcgcat gtggggaacc    900
acaaccatgt tcaaagccgt gttattggac aaagactgct ggatcactaa tatgcgactc    960
gatccaaaga caggactaga cccggagggg gttcgattac gcgccgctca gggattggaa   1020
gctgccgact actttgttca ggggtattgg gtatgggcgc ccattatcaa gaacttggca   1080
gccatcggat acgacaacaa caatatgcat ctcgcatcct atgactggag gttatcgttt   1140
gccaatctgg agaacagaga caagtacttt tcccgactga gtctaatct ggagctttcc    1200 ctcaaagtca caggggagaa aaatgtcctg gttgctcact ccatgggctc cacggtcctg   1260
ttttactttt tcaaatgggt cgaatctgag gaaggcggca agggcggacc caactgggtg   1320
aacgaccacg tacatacatt cgtcaacatt gcgggaccta tgctaggagt acccaagaca   1380
ctggctgctg tactttcagg agaggtacgg gatactgcac agctgggagt cgtcagcgca   1440
tacgttctgg aaaagttctt ttcgaggcgg gagcgggcgg acctgttcag gagctgggga   1500
ggactgacaa gcatgatccc caaggaggaa aaccgtatct ggggaacgat tcatggtgca   1560
ccggatgatg gaacccatga cgaggaggaa actttagtgc aggagaagat ctcaaagaac   1620
caggaggaac ccaatgctac gacgaagggc aagtggggcg acaaggaatc accgtccttt   1680
ggagcgatgc tggcatttgc agaaggttca gacatggagc atcacactat ggacgatagc   1740
atgaagctgc tttttaagac agctggcgat gattataatg ctatgctggc tgacaattac   1800
actgtcggcg cttcagtcac acaagcggag atggacaagt ccgacaaact ggctaccagc   1860
tggtccaacc ctctggaggc gacgcttcct aaggcgccca agatgaagat ttactgcctg   1920
tacggtgtcg gcaagtcgac cgagaggagc tatacgtaca accgtatgat cgacctcaca   1980
ccacagatct ttgaccaacg accaggaaat gtttcggacg aaactggcca ggtccccaag   2040
atttacatcg acacgtctgt tcacgacgag aagcttggta tcagctacgg tatccatcaa   2100
ggcgacggag atggaacggt cccattgctt tcaactggat acatgtgtgt agaagggtgg   2160
aacaagaagt tatataatcc ggccgggatc cagatcatca ctcgtgagtt tacgcaccag   2220
agcagtccct ctccggtaga tattcgtggg ggcaagagga cggcggacca tgtcgacatc   2280
ctaggcaact accaggtgac gaaggacctg ttaacgattg tagcgggacg ggatggcgat   2340
ggtctggaag agcagatata ctcgaagatt cgtgagtact ctgccaaggt cgacttgtga   2400
```

<210> SEQ ID NO 4
<211> LENGTH: 2457
<212> TYPE: DNA
<213> ORGANISM: Mortierella alpina

<400> SEQUENCE: 4

```
atggcttggc gagggcaact cacaatatcg tcgaccttga atattttcgg ctcagcgaat     60
tcaccagccg atatgatatc attgatttgt atatttcaac gattattgat ccactttcca    120
ttagatccac ctaaccgaca gacttcattc gaacatcctt caatggcacc gagaaagagg    180
aagcaggcca gtgaaatag gagcagcagc aactccagca caaatcccac caccaatact    240
caaatcagca gcgatgcaca taacgcacag gacacccatg acgctctcaa cacacatgcc    300
```

```
aacggaaagg gccccatgag ccaagttgag ccagaacccc actgcagcac caaagaagag    360
atcaaggatg ccatcgccaa gctgtccaac tcattaccca aagataccaa gatcgaggtc    420
aggcacccct ctctcagtcg caacccctct gtcggcgatt atctgcataa ggcgctgttc    480
gtgagtgagg ccgaggccaa gagccggaaa aaacacgtcg cccctgccac ccgccgtcgc    540
gtcatccttc tgcttggtat catcattggc atgggtctgg ccacagtctt gatgcggcag    600
tccaaggacg cagcctacat agaagccttc tcccactact ttcaggactt tgacctagcc    660
tccatggtcc cctctggcat gatcccagac gagttcattg ggaatgtatc agctatgttc    720
aagccagaga ttctgaccga ggaagagttc tatccaggag aggcactgcg atcggagcaa    780
ggttatagac ctaagcaccc tgttaccatg attcctggaa tcgtatcaac tggccttgag    840
tcttggtcaa caacacacaa ctgctcccag aaatacttcc ggaagcgcat gtggggaacc    900
acaaccatgt tcaaagccgt gttattggac aaagactgct ggatcactaa tatgcgactc    960
gatccaaaga caggactaga cccggagggg gttcgattac gcgccgctca gggattggaa   1020
gctgccgact actttgttca ggggtattgg gtatgggcgc ccattatcaa gaacttggca   1080
gccatcggat acgacaacaa caatatgcat ctcgcatcct atgactggag gttatcgttt   1140
gccaatctgg agaacagaga caagtacttt tcccgactga agtctaatct ggagcttttcc  1200 ctcaaagtca caggggagaa aaatgtcctg gttgctcact ccatgggctc acggtcctg   1260 ttttactttt tcaaatgggt cgaatctgag gaaggcggca agggcggacc caactgggtg   1320
aacgaccacg tacatacatt cgtcaacatt gcgggaccta tgctaggagt acccaagaca   1380
ctggctgctg tactttcagg agaggtacgg gatactgcac agctgggagt cgtcagcgca   1440
tacgttctgg aaaagttctt ttcgaggcgg gagcgggcgg acctgttcag gagctgggga   1500
ggactgacaa gcatgatccc caaggagga aaccgtatct ggggaacgat tcatggtgca   1560
ccggatgatg gaacccatga cgaggaggaa actttagtgc aggagaagat ctcaaagaac   1620
caggaggaac ccaatgctac gacgaagggc aagtggggcg acaaggaatc accgtccttt   1680
ggagcgatgc tggcatttgc agaaggttca gacatggagc atcacactat ggacgatagc   1740
atgaagctgc ttttttaagac agctggcgat gattataatg ctatgctggc tgacaattac   1800
actgtcggcg cttcagtcac acaagcggag atggacaagt ccgacaaact ggctaccagc   1860
tggtccaacc ctctggaggc gacgcttcct aaggcgccca agatgaagat ttactgcctg   1920
tacggtgtcg gcaagtcgac cgagaggagc tatacgtaca accgtatgat cgacctcaca   1980
ccacagatct ttgaccaacg accaggaaat gtttcggacg aaactggcca ggtccccaag   2040
atttacatcg acacgtctgt tcacgacgag aagcttggta tcagctacgg tatccatcaa   2100
ggcgacggag atggaacggt cccattgctt tcaactggat acatgtgtgt agaagggtgg   2160
aacaagaagt tatataatcc ggccgggatc cagatcatca ctcgtgagtt tacgcaccag   2220
agcagtccct ctccggtaga tattcgtggg ggcaagagga cggcggacca tgtcgacatc   2280
ctaggcaact accaggtgac gaaggacctg ttaacgattg tagcgggacg ggatggcgat   2340
ggtctggaag agcagatata ctcgaagatt cgtgagtact ctgccaaggt cgacttgtga   2400
taatttttag ctgtgcgcca ttaaaaaaaa ttagccgaaa aaaaaaaaaa aaaaaaa      2457
```

<210> SEQ ID NO 5
<211> LENGTH: 2949
<212> TYPE: DNA
<213> ORGANISM: Mortierella alpina

<400> SEQUENCE: 5

```
atggcttggc gagggcaact cacaatatcg tcgaccttga atattttcgg ctcagcgaat      60
tcaccagccg atatgatatc attgatttgt atatttcaac gattattgat ccactttcca     120
ttagatccac ctaaccgaca gacttcattc gaacatcctt caatggcacc gagaaagagg     180
aagcaggcca gtagaaatag gagcagcagc aactccagca caaatcccac caccaatact     240
caaatcagca gcgatgcaca taacgcacag acacccatg acgctctcaa cacacatgcc      300
aacgaaaagg gccccatgag ccaagttgag ccagaacccc actgcagcac caaagaagag     360
atcaaggatg ccatcgccaa gctgtccaac tcattaccca agataccaa gatcgaggtc      420
aggcacccct ctctcagtcg caaccctct gtcggcgatt atctgcataa ggcgctgttc       480
gtgagtgagg ccgaggccaa gagccggaaa aaacacgtcg ccctgccac cgccgtcgc       540
gtcatccttc tgcttggtat catcattggc atgggtctgg ccacagtctt gatgcggcag     600
tccaaggacg cagcctacat agaagccttc tcccactact ttcaggactt tgacctagcc     660
tccatggtcc cctctggcat gatcccagac gagttcattg gaatgtatc agctatgttc      720
aagccagaga ttctgaccga ggaagagttc tatccaggag aggcactgcg atcggagcaa     780
ggttatagac ctaagcaccc tgtaagagca tggacccttg tagcagtgag ttgcaatgcg     840
ttgacgggac cacgttagca acgattattt atgtctctgt gttgttttat gcattttgta    900
ggttaccatg attcctggaa tcgtatcaac tggccttgag tcttggtcaa caacacacaa     960
ctgctcccag aaatacttcc ggaagcgcat gtggggaacc acaagtaatg catctctttt    1020
caccgtggca gacttctttc tatgcgtatc gcgttgcaat cgttttgatc ctaacgtctc    1080
gttctctctc ctaatctagc catgttcaaa gccgtgttat tggacaaaga ctgctggatc    1140
actaatatgc gactcgatcc aaagacagga ctagacccgg aggggttcg attacgcgcc     1200
gctcagggat tggaagctgc cgactacttt gttcaggggt gagtgagcgc attgcgttgt    1260
tctttctgcg cacttttcac gtgcaaaaac tccatggata aaatggagac gacacagtgt    1320
taccgacact gcattaatca cgcgcgcctt gacgtttctt gcggtcatcg taggtattgg    1380
gtatgggcgc ccattatcaa ggtaaaactc gacagcacct gtcagaccgg tttctgtaa    1440
tgcctcgcgt gaatattcct atgctgacat tgtgtgcgac caattgtaga acttggcagc    1500
catcggatac gacaacaaca atatgcatct cgcatcctat gactggaggt tatcgtttgc    1560
caatctggag aacagagaca agtactttc ccgactgaag tctaatctgg agctttccct    1620
caaagtcaca ggggagaaaa atgtcctggt tgctcactcc atgggctcca cggtcctgtt    1680
ttactttttc aaatgggtcg aatctgagga aggcggcaag ggcggaccca actgggtgaa    1740
cgaccacgta catacattcg tcaacattgc gggacctatg ctaggagtac ccaagacact    1800
ggctgctgta ctttcaggag aggtacggga tactgcacag ctgggagtcg tcagcgcata    1860
cgttctggaa aagttctttt cgaggcggga gcggcggac ctgttcagga gctggggagg    1920
actgacaagc atgatcccca aaggaggaaa ccgtatctgg ggaacgattc atggtgcacc    1980
ggatgatgga acccatgacg aggaggaaac tttagtgcag gagaagatct caaagaacca    2040
ggaggaaccc aatgctacga cgaagggcaa gtgggggcgac aaggaatcac cgtcctttgg    2100
agcgatgctg gcatttgcag aaggttcaga catggagcat cacactatgg acgatagcat    2160
gaagctgctt tttaagacag ctggcgatga ttataatgct atgctggctg acaattacac    2220
tgtcggcgct tcagtcacac aagcggagat ggacaagtcc gacaaactgg ctaccagctg    2280
gtccaaccct ctggaggcga cgcttcctaa ggcgcccaag atgaagattt actgcctgta    2340
```

-continued

```
cggtgtcggc aagtcgaccg agaggagcta tacgtacaac cgtatgatcg acctcacacc    2400
acagatcttt gaccaacgac caggaaatgt ttcggacgaa actggccagg tccccaagat    2460
ttacatcgac acgtctgttc acgacgagaa gcttggtatc agctacggta tccatcaagg    2520
cgacgggtaa tgctcaatcg tcatttgctg ctactttgct attttgttga acttgattgt    2580
tcgtttctaa ttttcgatcc tcttgcccat tttactgtag agatggaacg gtcccattgc    2640
tttcaactgg atacatgtgt gtagaagggt ggaacaagaa gttatataat ccggccggga    2700
tccagatcat cactcgtgag tttacgcacc agagcagtcc ctctccggta gatattcgtg    2760
ggggcaagag gacggcggac catgtcgaca tcctaggcaa ctaccaggtg acgaaggacc    2820
tgttaacgat tgtagcggga cgggatggcg atggtctgga agagcagata tactcgaaga    2880
ttcgtgagta ctctgccaag gtcgacttgt gataattttt agctgtgcgc cattaaaaaa    2940
aattagccg                                                            2949
```

<210> SEQ ID NO 6
<211> LENGTH: 25
<212> TYPE: DNA
<213> ORGANISM: Artificial
<220> FEATURE:
<223> OTHER INFORMATION: Synthetic DNA

<400> SEQUENCE: 6
cctggaatcg tatcaactgg ccttg                                          25

<210> SEQ ID NO 7
<211> LENGTH: 23
<212> TYPE: DNA
<213> ORGANISM: Artificial
<220> FEATURE:
<223> OTHER INFORMATION: Synthetic DNA

<400> SEQUENCE: 7
caggtccgcc cgctcccgcc tcg                                            23

<210> SEQ ID NO 8
<211> LENGTH: 26
<212> TYPE: DNA
<213> ORGANISM: Artificial
<220> FEATURE:
<223> OTHER INFORMATION: Synthetic DNA

<400> SEQUENCE: 8
ctctcctgga tagaactctt cctcgg                                         26

<210> SEQ ID NO 9
<211> LENGTH: 23
<212> TYPE: DNA
<213> ORGANISM: Artificial
<220> FEATURE:
<223> OTHER INFORMATION: Synthetic DNA

<400> SEQUENCE: 9
atggcttggc gagggcaact cac                                            23

<210> SEQ ID NO 10
<211> LENGTH: 29
<212> TYPE: DNA
<213> ORGANISM: Artificial
<220> FEATURE:
<223> OTHER INFORMATION: Synthetic DNA

<400> SEQUENCE: 10

```
ggatccatgg cttggcgagg gcaactcac                                    29

<210> SEQ ID NO 11
<211> LENGTH: 30
<212> TYPE: DNA
<213> ORGANISM: Artificial
<220> FEATURE:
<223> OTHER INFORMATION: Synthetic DNA

<400> SEQUENCE: 11
gaattcatgt caggaacatt caatgatata                                   30

<210> SEQ ID NO 12
<211> LENGTH: 30
<212> TYPE: DNA
<213> ORGANISM: Artificial
<220> FEATURE:
<223> OTHER INFORMATION: Synthetic DNA

<400> SEQUENCE: 12
gtcgacttac ccaactatct tcaattctgc                                   30

<210> SEQ ID NO 13
<211> LENGTH: 30
<212> TYPE: DNA
<213> ORGANISM: Artificial
<220> FEATURE:
<223> OTHER INFORMATION: Synthetic DNA

<400> SEQUENCE: 13
gaattcatgg gcacactgtt tcgaagaaat                                   30

<210> SEQ ID NO 14
<211> LENGTH: 30
<212> TYPE: DNA
<213> ORGANISM: Artificial
<220> FEATURE:
<223> OTHER INFORMATION: Synthetic DNA

<400> SEQUENCE: 14
gtcgacttac attgggaagg gcatctgaga                                   30

<210> SEQ ID NO 15
<211> LENGTH: 24
<212> TYPE: DNA
<213> ORGANISM: Artificial
<220> FEATURE:
<223> OTHER INFORMATION: Synthetic DNA

<400> SEQUENCE: 15
gaccagtgtc atcagagaaa tagg                                         24

<210> SEQ ID NO 16
<211> LENGTH: 22
<212> TYPE: DNA
<213> ORGANISM: Artificial
<220> FEATURE:
<223> OTHER INFORMATION: Synthetic DNA

<400> SEQUENCE: 16
gagctggaac tgcctttgga gc                                           22

<210> SEQ ID NO 17
<211> LENGTH: 28
<212> TYPE: DNA
```

<213> ORGANISM: Artificial
<220> FEATURE:
<223> OTHER INFORMATION: Synthetic DNA

<400> SEQUENCE: 17
tctagaatgg cacctcccaa cactattg                                    28

<210> SEQ ID NO 18
<211> LENGTH: 30
<212> TYPE: DNA
<213> ORGANISM: Artificial
<220> FEATURE:
<223> OTHER INFORMATION: Synthetic DNA

<400> SEQUENCE: 18
aagcttttac ttcttgaaaa agaccacgtc                                  30

<210> SEQ ID NO 19
<211> LENGTH: 29
<212> TYPE: DNA
<213> ORGANISM: Artificial
<220> FEATURE:
<223> OTHER INFORMATION: Synthetic DNA

<400> SEQUENCE: 19
tctagaatgg ctgctgctcc cagtgtgag                                   29

<210> SEQ ID NO 20
<211> LENGTH: 29
<212> TYPE: DNA
<213> ORGANISM: Artificial
<220> FEATURE:
<223> OTHER INFORMATION: Synthetic DNA

<400> SEQUENCE: 20
aagcttttac tgtgccttgc ccatcttgg                                   29

<210> SEQ ID NO 21
<211> LENGTH: 28
<212> TYPE: DNA
<213> ORGANISM: Artificial
<220> FEATURE:
<223> OTHER INFORMATION: Synthetic DNA

<400> SEQUENCE: 21
tctagaatgg agtcgattgc gcaattcc                                    28

<210> SEQ ID NO 22
<211> LENGTH: 30
<212> TYPE: DNA
<213> ORGANISM: Artificial
<220> FEATURE:
<223> OTHER INFORMATION: Synthetic DNA

<400> SEQUENCE: 22
gagctcttac tgcaacttcc ttgccttctc                                  30

<210> SEQ ID NO 23
<211> LENGTH: 30
<212> TYPE: DNA
<213> ORGANISM: Artificial
<220> FEATURE:
<223> OTHER INFORMATION: Synthetic DNA

<400> SEQUENCE: 23
tctagaatgg gtgcggacac aggaaaaacc                                  30

-continued

```
<210> SEQ ID NO 24
<211> LENGTH: 30
<212> TYPE: DNA
<213> ORGANISM: Artificial
<220> FEATURE:
<223> OTHER INFORMATION: Synthetic DNA

<400> SEQUENCE: 24
aagcttttac tcttccttgg gacgaagacc                                    30

<210> SEQ ID NO 25
<211> LENGTH: 20
<212> TYPE: DNA
<213> ORGANISM: Artificial
<220> FEATURE:
<223> OTHER INFORMATION: Synthetic DNA

<400> SEQUENCE: 25
cgcatcccgc aaacacacac                                               20

<210> SEQ ID NO 26
<211> LENGTH: 24
<212> TYPE: DNA
<213> ORGANISM: Artificial
<220> FEATURE:
<223> OTHER INFORMATION: Synthetic DNA

<400> SEQUENCE: 26
ggcggaccca actgggtgaa cgac                                          24

<210> SEQ ID NO 27
<211> LENGTH: 25
<212> TYPE: DNA
<213> ORGANISM: Artificial
<220> FEATURE:
<223> OTHER INFORMATION: Synthetic DNA

<400> SEQUENCE: 27
tcacaagtcg accttggcag agtac                                         25
```

DIACYLGLYCEROL ACYLTRANSFERASE GENES AND USE THEREOF

TECHNICAL FIELD

The present invention relates to a polynucleotide encoding a novel diacylglycerol acyltransferase and a method for use thereof.

BACKGROUND ART

Triacylglycerols, which are storage lipids, are produced by the transfer of acyl moieties on diacylglycerols. Enzymes that transfer an acyl group to a diacylglycerol are called diacylglycerol acyltransferases (DGATs), and there are known an acyl-CoA:diacylglycerol acyltransferase (EC 2.3.1.20) of a type where acyl CoA serves an acyl donor and a phospholipid:diacylglycerol acyltransferase:PDAT (EC 2.3.1.158) of a type where a phospholipid serves an acyl donor.

DGAT which uses acyl CoA as an acyl donor is classified into 2 families of DGAT1 and DGAT2 due to differences in primary structure (Non-Patent Documents 1 and 2). Also, PDAT genes are cloned from yeast, plants, etc. (Patent Document 1 and Non-Patent Documents 3 and 4). Among them, it is known that PDAT derived from *Arabidopsis* utilizes as an acyl donor various phospholipids including phosphatidic acid, phosphatidylcholine, phosphatidylethanolamine, etc. and can transfer acyl residues ranging from $C_{10}$-$C_{22}$ (Non-Patent Document 5).

In the yeast *Saccharomyces cerevisiae* in which studies are relatively advanced in fungi, DGA1 (YOR245C) belonging to the DGAT2 family (Non-Patent Document 6) and LRO1 (YNR008W) which is PDAT are known as DGAT-encoding genes. The enzyme which is encoded by these two genes accounts for a large part of the DGAT activity in the yeast but even when these genes are simultaneously disrupted, the DGAT activity is not completely lost. It is known that the DGAT activity of the enzyme encoded by the ARE1 and ARE2 genes, which are acyl CoA:sterol acyltransferase genes, contributes to this remaining DGAT activity (Non-Patent Document 7).

With respect to *Mortierella alpina* (*M. alpina*), which is a lipid-producing fungus, 4 types of DGATs and their genes which utilize acyl CoA as an acyl donor are reported (two types of DGAT1 family genes and two types of DGAT2 family genes) (Patent Documents 2 and 3 and Non-Patent Document 8).

However, homologs of PDAT which uses a phospholipid as an acyl donor are unknown in *M. alpina*. A Δ5 fatty acid desaturase is an enzyme which catalyzes the oxidation of dihomo-γ-linolenic acid (DGLA) to form arachidonic acid (ARA). It is known in *M. alpina* that since the enzyme acts mainly on DGLA present as the acyl residues of phosphatidylcholine, arachidonic acid is formed as the acyl residues of phosphatidylcholine (Non-Patent Document 9). Therefore, enzymes for the synthesis of arachidonic acid-containing triacylglycerols from arachidonic acid present as the acyl residues of phospholipids such as phosphatidylcholine, etc. are required to promote the formation of triacylglycerols containing arachidonic acid.

PATENT DOCUMENTS

[Patent Document 1] Japanese Unexamined Patent Application Publication (Translation of PCT Application) No. 2002-541783
[Patent Document 2] U.S. 2006/0094086
[Patent Document 3] U.S. 2006/0091087

NON-PATENT DOCUMENTS

[Non-Patent Document 1] Proc. Natul. Acad. Sci. USA, 95, 13018-13023, 1998
[Non-Patent Document 2] J.B.C., 276 (42), 38862-38869, 2001
[Non-Patent Document 3] J.B.C., 275 (21), 15609-15612, 2000
[Non-Patent Document 4] Proc. Natl. Acd. Sci. USA, 97(12), 6487-6492
[Non-Patent Document 5] Plant Physiology, 135, 1324-1335
[Non-Patent Document 6] J. Bacteriol., 184, 519-524, 2002
[Non-Patent Document 7] J.B.C., 277(8), 6478-6482, 2002
[Non-Patent Document 8] Collected Abstract of the 2003 Annual Meeting of The Japan Society for Agricultural and Biological Chemistry
[Non-Patent Document 9] J.B.C., 278(37), 35115-35126, 2003

DISCLOSURE OF THE INVENTION

Under the foregoing circumstances, there is a need for a novel enzyme which is useful for producing triacylglycerols containing arachidonic acid in *M. alpina*.

As a result of extensive studies, the present inventors have succeeded in cloning a gene encoding the PDAT homolog (MaLRO1) from *M. alpina* which is a lipid-producing fungus. The present invention has thus been accomplished. More specifically, the present invention provides the following polynucleotides, proteins, expression vectors, transformants, a method for producing lipid or fatty acid compositions as well as food products, using the transformants, food products or the like produced by the method, and so on.

That is, the present invention provides the following features, and so on.

[1] A polynucleotide according to any one selected from the group consisting of (a) to (e) below:
(a) a polynucleotide comprising the nucleotide sequence of SEQ ID NO: 1 or 4;
(b) a polynucleotide encoding a protein consisting of the amino acid sequence of SEQ ID NO: 2;
(c) a polynucleotide encoding a protein consisting of an amino acid sequence wherein 1 to 100 amino acids are deleted, substituted, inserted and/or added in the amino acid sequence of SEQ ID NO: 2, and having a diacylglycerol acyltransferase activity;
(d) a polynucleotide encoding a protein having an amino acid sequence having at least 60% homology to the amino acid sequence of SEQ ID NO: 2, and having a diacylglycerol acyltransferase activity; and,
(e) a polynucleotide which hybridizes to a polynucleotide consisting of a nucleotide sequence complementary to the nucleotide sequence of SEQ ID NO: 1 or 4 under stringent conditions, and which encodes a protein having a diacylglycerol acyltransferase activity.

[2] The polynucleotide according to [1] above, which is either one defined in (f) or (g) below:
(f) a polynucleotide encoding a protein consisting of an amino acid sequence wherein 1 to 10 amino acids are deleted, substituted, inserted and/or added in the amino acid sequence of SEQ ID NO: 2, and having a diacylglycerol acyltransferase activity; and,
(g) a polynucleotide encoding a protein having an amino acid sequence having at least 75% homology to the amino acid sequence of SEQ ID NO: 2, and having a diacylglycerol acyltransferase activity.

[3] The polynucleotide according to [1] above, comprising the nucleotide sequence of SEQ ID NO: 1 or 4.

[4] The polynucleotide according to [1] above, encoding a protein consisting of the amino acid sequence of SEQ ID NO: 2.

[5] The polynucleotide according to any one of [1] to [4] above, which is a DNA.

[6] A protein encoded by the polynucleotide according to any one of [1] to [5] above.

[7] A vector comprising the polynucleotide according to any one of [1] to [5] above.

[8] A non-human transformant introduced with the polynucleotide according to any one of [1] to [5] above.

[9] A non-human transformant introduced with the vector according to [7] above.

[10] The transformant according to [8] or [9] above, wherein the transformant is a lipid-producing fungus.

[11] The transformant according to [10] above, wherein the lipid-producing fungus is *Mortierella alpina*.

[12] A method for producing a lipid or fatty acid composition, which comprises collecting the lipid or fatty acid composition from the culture of the transformant according to any one of [8] to [11] above.

[13] The method according to [12] above, wherein the lipid is a triacylglycerol.

[14] The method according to [12] above, wherein the fatty acid is arachidonic acid or dihomo-γ-linolenic acid.

[15] A food product, pharmaceutical, cosmetic or soap comprising the lipid or fatty acid composition collected by the production method according to [12] above.

The polynucleotide of the present invention can be used for transformation of a lipid-producing fungus (e.g., *M. alpina*), yeast, plant, etc. That is, the polynucleotide of the present invention is introduced into an appropriate host cell to obtain a transformant and the polynucleotide above is expressed in the transformant, whereby DGLA or ARA-rich triacylglycerols can be efficiently produced. The transformant (lipid-producing fungus transformant, yeast transformant, plant transformant, etc.) thus produced can be used to produce fatty acid compositions, food products, cosmetics, pharmaceuticals, soaps, etc.

More specifically, the transformant of the present invention provides an extremely high production efficiency of lipids and fatty acids. Accordingly, the present invention can be effectively used to manufacture medicaments or health foods which require a large quantity of lipids or fatty acids.

BRIEF DESCRIPTION OF DRAWINGS

FIG. 1A shows the alignment between the genome sequence and CDS sequence of MaLRO1.

FIG. 1B shows the alignment between the genome sequence and CDS sequence of MaLRO1, which is continued from FIG. 1A.

FIG. 2A shows the CDS sequence of MaLRO1 and its putative amino acid sequence.

FIG. 2B shows the CDS sequence of MaLRO1 and its putative amino acid sequence, which is continued from FIG. 2A.

FIG. 3 shows the alignment between the amino acid sequences of PDAT homologous proteins from various fungi. The amino acid residues (marked with *) considered to be important for the PDAT activity were conserved beyond the fungal species.

FIG. 4 shows the fatty acid content in the lipid fraction extracted from yeast cells.

FIG. 5 shows the fatty acid composition in the lipid fraction extracted from yeast cells.

BEST MODE FOR CARRYING OUT THE INVENTION

Hereinafter the present invention is described in detail. The embodiments below are intended to be merely by way of example only to describe the invention but not limited only to these embodiments. The present invention may be implemented in various ways without departing from the gist of the invention.

All of the publications, published patent applications, patents and other patent documents cited in this application are herein incorporated by reference in their entirety. This application hereby incorporates by reference the contents of the specification and drawings in the Japanese Patent Application (No. 2009-289287) filed Dec. 21, 2009, from which the priority was claimed.

The present inventors have succeeded for the first time in cloning the gene of the full-length cDNA of gene (MaLRO1) for the homologues of PDAT derived from the lipid-producing fungus *M. alpina*, as will be later described in detail in EXAMPLES below. The present inventors have also identified the nucleotide sequence of genomic DNA of MaLRO1 from *M. alpina* and its putative amino acid sequence. The ORF sequence of MaLRO1, the putative amino acid sequence of MaLRO1, the CDS sequence of MaLRO1, the cDNA sequence of MaLRO1 and the genome sequence of MaLRO1 are SEQ ID NO: 1, SEQ ID NO: 2, SEQ ID NO: 3, SEQ ID NO: 4 and SEQ ID NO: 5, respectively. These polynucleotides and enzymes may be obtained by the methods described in EXAMPLES below, known genetic engineering techniques, known methods for synthesis, and so on.

1. Polynucleotide of the Invention

First, the present invention provides the polynucleotide described in any one selected from the group consisting of (a) to (e) below:

(a) a polynucleotide comprising the nucleotide sequence of SEQ ID NO: 1 or 4;

(b) a polynucleotide encoding a protein consisting of the amino acid sequence of SEQ ID NO: 2;

(c) a polynucleotide encoding a protein consisting of an amino acid sequence wherein 1 to 100 amino acids are deleted, substituted, inserted and/or added in the amino acid sequence of SEQ ID NO: 2, and having a diacylglycerol acyltransferase activity;

(d) a polynucleotide encoding a protein having an amino acid sequence having at least 85% homology to the amino acid sequence of SEQ ID NO: 2, and having a diacylglycerol acyltransferase activity; and, (e) a polynucleotide which hybridizes to a polynucleotide consisting of a nucleotide sequence complementary to the nucleotide sequence of SEQ ID NO: 1 or 4 under stringent conditions, and which encodes a protein having a diacylglycerol acyltransferase activity.

As used herein, the term "polynucleotide" means a DNA or RNA.

As used herein, the term "polynucleotide which hybridizes under stringent conditions" refers to a polynucleotide obtained by a colony hybridization method, a plaque hybridization method, a Southern hybridization method or the like, using as a probe, for example, a polynucleotide consisting of a nucleotide sequence complementary to the nucleotide sequence of SEQ ID NO: 1 or 4, or the whole or part of a polynucleotide consisting of the nucleotide sequence encoding the amino acid sequence of SEQ ID NO: 2. For the methods of hybridization, there are used the methods described in, e.g., "Sambrook & Russell, Molecular Cloning; A Laboratory Manual Vol. 3, Cold Spring Harbor, Laboratory Press 2001" and "Ausubel, Current Protocols in Molecular Biology, John Wiley & Sons 1987-1997", etc.

As used herein, the term "stringent conditions" may be any of low stringent conditions, moderate stringent conditions or high stringent conditions. The term "low stringent conditions" are, for example, 5×SSC, 5×Denhardt's solution, 0.5% SDS, 50% formamide at 32° C. The term "moderate stringent conditions" are, for example, 5×SSC, 5×Denhardt's solution, 0.5% SDS, 50% formamide at 42° C., or 5×SSC, 1% SDS, 50 mM Tris-HCl (pH 7.5), 50% formamide at 42° C. The term "high stringent conditions" are, for example, 5×SSC, 5×Denhardt's solution, 0.5% SDS, 50% formamide at 50° C. or 0.2×SSC, 0.1% SDS at 65° C. Under these conditions, a DNA with higher homology is expected to be obtained efficiently at higher temperatures, although multiple factors are involved in hybridization stringency including temperature, probe concentration, probe length, ionic strength, time, salt concentration and others, and one skilled in the art may appropriately select these factors to achieve similar stringency.

When commercially available kits are used for hybridization, for example, an Alkphos Direct Labeling and Detection System (GE Healthcare) may be used. In this case, according to the attached protocol, after cultivation with a labeled probe overnight, the membrane is washed with a primary wash buffer containing 0.1% (w/v) SDS at 55° C., thereby detecting hybridized DNA. Alternatively, in producing a probe based on the nucleotide sequence complementary to the nucleotide sequence of SEQ ID NO: 1 or 4 or on the entire or part of the nucleotide sequence encoding the amino acid sequence of SEQ ID NO: 2, hybridization can be detected with a DIG Nucleic Acid Detection Kit (Roche Diagnostics) when the probe is labeled with digoxygenin (DIG) using a commercially available reagent (e.g., a PCR Labeling Mix (Roche Diagnostics), etc.).

In addition to those described above, other polynucleotides that can be hybridized include DNAs having 50% or higher, 51% or higher, 52% or higher, 53% or higher, 54% or higher, 55% or higher, 56% or higher, 57% or higher, 58% or higher, 59% or higher, 60% or higher, 61% or higher, 62% or higher, 63% or higher, 64% or higher, 65% or higher, 66% or higher, 67% or higher, 68% or higher, 69% or higher, 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher or 99.9% or higher identify with to the DNA of SEQ ID NO: 1 or 4, or the DNA encoding the amino acid sequence of SEQ ID NO: 2, as calculated by homology search software, such as FASTA and BLAST using default parameters.

Identity between amino acid sequences or nucleotide sequences may be determined using algorithm BLAST by Karlin and Altschul (Proc. Natl. Acad. Sci. USA, 87: 2264-2268, 1990; Proc. Nail Acad. Sci. USA, 90: 5873, 1993). Programs called BLASTN, BLASTX, BLASTP, tBLASTN and tBLASTX based on the BLAST algorithm have been developed (Altschul S. F. et al., J. Mol. Biol. 215: 403, 1990). When a nucleotide sequence is sequenced using BLASTN, the parameters are, for example, score=100 and wordlength=12. When an amino acid sequence is sequenced using BLASTP, the parameters are, for example, score=50 and wordlength=3. When BLAST and Gapped BLAST programs are used, default parameters for each of the programs are employed.

The polynucleotides of the present invention described above can be acquired by known genetic engineering techniques, known methods for synthesis, and so on.

2. Protein of the Invention

The present invention provides the proteins shown below.

(i) A protein encoded by the polynucleotide of any one of (a) to (e) above.

(ii) A protein comprising the amino acid sequence of SEQ ID NO: 2.

(iii) A protein containing an amino acid sequence wherein one or more amino acids are deleted, substituted, inserted and/or added in the amino acid sequence of SEQ ID NO: 2, and having a diacylglycerol acyltransferase activity.

(iv) A protein having an amino acid sequence having at least 60% homology to the amino acid sequence of SEQ ID NO: 2, and having a diacylglycerol acyltransferase activity.

The proteins described in (iii) or (iv) above are typically naturally occurring mutants of protein of SEQ ID NO: 2 and include those proteins which may be artificially obtained using site-directed mutagenesis described in, e.g., "Sambrook & Russell, Molecular Cloning: A Laboratory Manual, Vol. 3, Cold Spring Harbor Laboratory Press 2001," "Ausubel, Current Protocols in Molecular Biology, John Wiley & Sons 1987-1997," "Nuc. Acids. Res., 10, 6487 (1982)," "Proc. Natl. Acad. Sci. USA, 79, 6409 (1982)," "Gene, 34, 315 (1985)," "Nuc. Acids. Res., 13, 4431 (1985)," "Proc. Natl. Acad. Sci. USA, 82, 488 (1985)," etc.

As used herein, "the protein containing an amino acid sequence wherein one or more amino acids are deleted, substituted, inserted and/or added in the amino acid sequence of SEQ ID NO: 2, and having a diacylglycerol acyltransferase activity" includes proteins containing an amino acid sequence wherein, e.g., 1 to 100, 1 to 90, 1 to 80, 1 to 70, 1 to 60, 1 to 50, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9 (1 to several), 1 to 8, 1 to 7, 1 to 6, 1 to 5, 1 to 4, 1 to 3, 1 to 2, or one amino acid is/are deleted, substituted, inserted and/or added in the amino acid sequence of SEQ ID NO: 2, and having the diacylglycerol acyltransferase activity. In general, the number of deletions, substitutions, insertions, and/or additions is preferably smaller.

Such proteins include a protein having an amino acid sequence having the homology of approximately 60% or higher, 61% or higher, 62% or higher, 63% or higher, 64% or higher, 65% or higher, 66% or higher, 67% or higher, 68% or higher, 69% or higher, 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher, or 99.9% or higher, to the amino acid sequence of SEQ ID NO: 2, and having the diacylglycerol acyltransferase activity. As the homology percentage described above is higher, the protein is preferable in general.

The diacylglycerol acyltransferase activity can be assayed, e.g., by the method described in Stahl et al., Plant Physiology, 135, 1324-1335 (2004).

The diacylglycerol acyltransferase activity can also be confirmed by an experiment using the Δdga1, Δlro1 strains of yeast having decreased levels of triacylglycerol production. When a polynucleotide encoding the enzyme is expressed in the Δdga1, Δlro1 strains and the level of triacylglycerol produced increases, the protein or peptide encoded by the polynucleotide is found to have the diacylglycerol acyltransferase activity. In EXAMPLES, the present inventors fractionated lipids into the triacylglycerol (TG) fraction and the phospholipid (PL) fraction and confirmed an increase in the level of triacylglycerol produced. However, no change was observed in the level of phospholipids produced (FIG. 4).

In the present invention, the diacylglycerol acyltransferase activity may be either acyl CoA:diacylglycerol acyltransferase activity or phospholipids:diacylglycerol acyltransferase activity, and preferably, phospholipid:diacylglycerol acyltransferase activity.

The deletion, substitution, insertion and/or addition of one or more amino acid residues in an amino acid sequence of the protein of the invention means that one or a plurality of amino acid residues are deleted, substituted, inserted and/or added at one or a plurality of positions in the same amino acid sequence. Two or more types of deletions, substitutions, insertions and additions may occur at the same time.

Examples of the amino acid residues which are mutually substitutable are given below. Amino acid residues in the same group are mutually substitutable. Group A: leucine, isoleucine, norleucine, valine, norvaline, alanine, 2-aminobutanoic acid, methionine, o-methylserine, t-butylglycine, t-butylalanine and cyclohexylalanine; Group B: aspartic acid, glutamic acid, isoaspartic acid, isoglutamic acid, 2-aminoadipic acid and 2-amino suberic acid; Group C: asparagine and glutamine; Group D: lysine, arginine, ornithine, 2,4-diaminobutanoic acid and 2,3-diaminopropionic acid; Group E: proline, 3-hydroxyproline and 4-hydroxyproline; Group F: serine, threonine and homoserine; and Group G: phenylalanine and tyrosine.

The protein of the present invention may also be produced by chemical synthesis methods such as the Fmoc method (fluorenylmethyloxycarbonyl method), the tBoc method (t-butyloxycarbonyl method), etc. In addition, peptide synthesizers available from Advanced Automation Peptide Protein Technologies, Perkin Elmer, Protein Technology Instrument, PerSeptive, Applied Biosystems, SHIMADZU Corp., etc. may also be used for the chemical synthesis.

3. Vector of the Invention and Vector-Introduced Transformants

In another embodiment, the present invention also provides the expression vector comprising the polynucleotide of the invention.

The vector of the invention is generally constructed to contain an expression cassette comprising:
(i) a promoter that can be transcribed in a host cell;
(ii) any of the polynucleotides described in (a) to (g) above that is linked to the promoter; and,
(iii) an expression cassette comprising as a component a signal that functions in the host cell with respect to the transcription termination and polyadenylation of RNA molecule.

The vector thus constructed is introduced into a host cell. Examples of host cells which may be appropriately used in the present invention include lipid-producing fungi, yeast, and the like.

The lipid-producing fungi which can be used are the strains described in, e.g., MYCOTAXON, Vol. XLIV, No. 2, pp. 257-265 (1992). Specific examples include microorganisms belonging to the genus *Mortierella* including microorganisms belonging to the subgenus *Mortierella*, e.g., *Mortierella elongata* IFO8570, *Mortierella exigua* IFO8571, *Mortierella hygrophila* IFO5941, *Mortierella alpina* IFO8568, ATCC16266, ATCC32221, ATCC42430, CBS 219.35, CBS224.37, CBS250.53, CBS343.66, CBS527.72, CBS528.72, CBS529.72, CBS608.70 and CBS754.68, etc., or microorganisms belonging to the subgenus *Micromucor*, e.g., *Mortierella isabellina* CBS194.28, IFO6336, IFO7824, IFO7873, IFO7874, IFO8286, IFO8308 and IFO7884, *Mortierella nana* IFO8190, *Mortierella ramanniana* IFO5426, IFO8186, CBS112.08, CBS212.72, IFO7825, IFO8184, IFO8185 and IFO8287, *Mortierella vinacea* CBS236.82, etc. Among others, *Mortierella alpina* is preferable.

Examples of the yeast are *Saccharomyces cerevisiae* NBRC1951, NBRC1952, NBRC1953, NBRC1954, etc.

In introducing the vector of the invention into the yeast and assaying the diacylglycerol acyltransferase activity of the protein encoded by the vector, deficiency of the diacylglycerol acyltransferase genes (DGA1 and LRO1) of yeast used as a host cell enables to assess only the enzyme activity of the protein. Accordingly, in an embodiment of the present invention, the yeast as a host cell is preferably deficient of the DGA1 gene and the LRO1 gene.

These host cells transformed by the vector of the invention produce larger amounts of lipids, preferably triacylglycerols (also called "triglycerides"), more preferably, triacylglycerols containing arachidonic acid or DGLA, and most preferably, triacylglycerols containing arachidonic acid, as compared to the host cells that are not transformed by the vector of the invention.

Vectors used to introduce into the lipid-producing fungi include but not limited to, for example, pDura5 (Appl. Microbiol. Biotechnol., 65, 419-425, (2004)).

Any vector is usable as a vector used for introduction into the yeast and not particularly limited, so long as it is a vector capable of expressing the insert in the yeast cells, and includes, e.g., pYE22m (Biosci. Biotech. Biochem., 59, 1221-1228, 1995). The vector used to introduce into *Mortierella alpina* is not particularly limited as far as it is a vector capable of expressing the insert in *Mortierella alpina* cells, and an example includes vector pDuraMCS for *M. alpina* expression.

Promoters/terminators for regulating gene expression in host cells may be in an optional combination as far as they function in the host cells. For example, a promoter of the histone H4.1 gene, a promoter of the glyceraldehyde-3-phosphate dehydrogenase, etc. can be used.

As a selection marker used for the transformation, there may be used auxotrophic markers (ura5, niaD), chemical-resistant markers (hygromycin, zeocin), geneticin-resistant gene (G418r), copper-resistant gene (CUP1) (Marin et al., Proc. Natl. Acad. Sci. USA, 81, 337 1984), cerulenin-resistant gene (fas2m, PDR4) (Junji Inokoshi, et al., Biochemistry, 64, 660, 1992; and Hussain et al., Gene, 101: 149, 1991, respectively).

For transformation of host cells, there may be used generally known methods. For example, in transformation of lipid-producing fungi, electroporation method (Mackenzie D. A. et al., Appl. Environ. Microbiol., 66, 4655-4661, 2000) and the particle delivery method (method described in JPA 2005-287403 "Method of Breeding Lipid-Producing Fungus") may be used. On the other hand, in transformation of yeast, electroporation method, the spheroplast method (Proc. Natl. Acad. Sci. USA, 75 p 1929 (1978)), and the lithium acetate method (J. Bacteriology, 153 p 163 (1983)), and methods described in Proc. Natl. Acad. Sci. USA, 75 p 1929 (1978), Methods in yeast genetics, 2000 Edition: A Cold Spring Harbor Laboratory Course Manual, etc) may be used.

In addition, reference may be made to "Sambrook & Russell, Molecular Cloning: A Laboratory Manual Vol. 3, Cold Spring Harbor Laboratory Press 2001," "Methods in Yeast Genetics, A laboratory manual (Cold Spring Harbor Laboratory Press, Cold Spring Harbor, N.Y.)," etc. for general cloning techniques.

4. Method for Producing Lipid or Fatty Acid Composition of the Invention

In another embodiment, the present invention further provides a method for preparing a lipid or fatty acid composition which comprises using the lipid-producing fungus or yeast transformant described above.

As used herein, the term "lipid" is intended to mean a simple lipid including a compound which is composed of a fatty acid and an alcohol attached via an ester linkage (e.g., a glyceride), or its analog (e.g., a cholesterol ester), etc.; a complex lipid in which phosphoric acid, amino acid(s), saccharide(s) or the like are bound to a part of the simple lipid; or a derived lipid which is a hydrolysate of the above lipid and is insoluble in water.

As used herein, the term "oil and fat" is intended to mean an ester of glycerol and a fatty acid (glyceride).

As used herein, the term "fatty acid" is intended to mean an aliphatic monocarboxylic acid (a carboxylic acid having one carboxylic group and carbon atoms connected to each other in a chain) represented by general formula RCOOH (wherein R is an alkyl). The fatty acid includes a saturated fatty acid having no double bond and an unsaturated fatty acid containing a double bond(s) in the hydrocarbon chain.

The lipid or fatty acid composition of the present invention can be extracted from the cells transformed according to the present invention in the following manner. A transformant of an organism (e.g., a lipid-producing fungus or yeast) is cultured and then treated in a conventional manner, e.g., by centrifugation or filtration, etc. to obtain cultured cells. The cells are thoroughly washed with water and preferably dried. Drying may be accomplished by lyophilization, air-drying, etc. The dried cells are optionally destructed with a Dynomil or by ultrasonication, and then extracted with an organic solvent preferably in a nitrogen flow. Examples of the organic solvent available for use include ether, hexane, methanol, ethanol, chloroform, dichloromethane, petroleum ether and so on. Alternatively, good results can also be obtained by alternating extraction with methanol and petroleum ether or by extraction with a single-phase solvent system of chloroform-methanol-water. When the organic solvent is distilled off from the extract under reduced pressure, fatty acid-containing lipids can be obtained. The fatty acids extracted may be converted into the methyl esters by the hydrochloric acid methanol method, etc.

Moreover, the fatty acids can be separated in a state of mixed fatty acids or mixed fatty acid esters from the above fatty acid-containing lipids by concentration and separation in a conventional manner (e.g., urea addition, separation under cooling, column chromatography, etc.).

The lipids produced by the method of the present invention are preferably triacylglycerols, more preferably, triacylglycerols containing arachidonic acid or dihomo-γ-linolenic acid, and most preferably, triacylglycerols containing arachidonic acid.

The fatty acids produced by the method of the present invention are preferably arachidonic acid or dihomo-γ-linolenic acid, and most preferably, arachidonic acid. The lipid content produced by the method of the present invention and the fatty acid components contained in the lipid can be confirmed by the extraction method of lipids or separation method of fatty acids described above, or a combination thereof.

The lipid or fatty acid composition obtained by the production method of the present invention can be used to produce, e.g., food products, pharmaceuticals, industrial materials (raw materials for cosmetics, soaps, etc.) containing oils and fats, and the like.

In a still other embodiment, the present invention provides a method for preparing food products, cosmetics, pharmaceuticals, soaps, etc. using the lipid-producing fungus transformant or yeast transformant of the present invention. The method involves the step of forming lipids or fatty acids using the lipid-producing fungus transformant or yeast transformant of the present invention. Food products, cosmetics, pharmaceuticals, soaps, etc. containing the lipids or fatty acids formed are prepared in a conventional manner. As such, the food products, cosmetics, pharmaceuticals, soaps, etc. prepared by the method of the present invention contain the lipids or fatty acids produced using the lipid-producing fungus transformant or yeast transformant of the present invention. The present invention further provides the food products, cosmetics, pharmaceuticals, soaps, etc. prepared by the method.

The form of the cosmetic (composition) or pharmaceutical (composition) of the present invention is not particularly limited and may be any form including the state of a solution, paste, gel, solid or powder. Also, the cosmetic composition or pharmaceutical composition of the present invention may be used as cosmetics or topical agents for the skin, including an oil, lotion, cream, emulsion, gel, shampoo, hair rinse, hair conditioner, enamel, foundation, lipstick, face powder, facial pack, ointment, perfume, powder, eau de cologne, tooth paste, soap, aerosol, cleansing foam, etc., an anti-aging skin care agent, anti-inflammatory agent for the skin, bath agent, medicated tonic, skin beauty essence, sun protectant, or protective and improving agent for skin troubles caused by injury, chapped or cracked skin, etc.

The cosmetic composition of the present invention may further be formulated appropriately with other oils and fats and/or dyes, fragrances, preservatives, surfactants, pigments, antioxidants, etc., if necessary. The formulation ratio of these materials may be appropriately determined by those skilled in the art, depending upon purpose (for example, oils and fats may be contained in the composition in 1 to 99.99 wt %, preferably, 5 to 99.99 wt %, and more preferably, 10 to 99.95 wt %). If necessary, the pharmaceutical composition of the present invention may also contain other pharmaceutically active components (e.g., anti-inflammatory components) or aid components (e.g., lubricant or carrier components). Examples of the other components commonly used in a cosmetic or a skin preparation for external use include an agent for acne, an agent for preventing dandruff or itching, an antiperspirant and deodorant agent, an agent for burn injury, an anti-mite and lice agent, an agent for softening keratin, an agent for xeroderma, an antiviral agent, a percutaneous absorption promoting agent, and the like.

The food product of the present invention includes a dietary supplement, health food, functional food, food product for young children, baby food, infant modified milk, premature infant modified milk, geriatric food, etc. As used herein, the food or food product is intended to mean a solid, fluid and liquid food as well as a mixture thereof, and collectively means an edible stuff.

The term dietary supplement refers to food products enriched with specific nutritional ingredients. The term health food refers to food products that are healthful or good for health, and encompasses dietary supplements, natural foods and diet foods. The term functional food refers to a food product for replenishing nutritional ingredients which assist body control functions. Functional foods are synonymous with foods for specified health use. The term food for young children refers to a food product given to children up to about 6 years old. The term geriatric food refers to a food product treated to facilitate digestion and absorption when compared to untreated foods. The term infant modified milk refers to modified milk given to children up to about one year old. The term premature infant modified milk refers to modified milk given to premature infants until about 6 months after birth.

These food products include natural foods (treated with fats and oils) such as meat, fish and nuts; foods supplemented with fats and oils during cooking, e.g., Chinese foods, Chinese noodles, soups, etc.; foods prepared using fats and oils as heating media, e.g., tempura or deep-fried fish and vegetables, deep-fried foods, fried bean curd, Chinese fried rice, doughnuts, Japanese fried dough cookies or karinto; fat- and oil-based foods or processed foods supplemented with fats and oils during processing, e.g., butter, margarine, mayonnaise, dressing, chocolate, instant noodles, caramel, biscuits, cookies, cake, ice cream; and foods sprayed or coated with fats and oils upon finishing, e.g., rice crackers, hard biscuits, sweet bean paste bread, etc. However, the food product is not limited to foods containing fats and oils, and other examples include agricultural foods such as bakery products, noodles, cooked rice, sweets (e.g., candies, chewing gums, gummies, tablets, Japanese sweets), bean curd and processed products thereof; fermented foods such as Japanese rice wine or sake, medicinal liquor, sweet cooking sherry (mirin), vinegar, soy sauce and miso or bean paste, etc.; livestock food products such as yoghurt, ham, bacon, sausage, etc.; seafood products such as minced and steamed fish cake or kamaboko, deep-fried fish cake or ageten and puffy fish cake or hanpen, etc.; as well as fruit drinks, soft drinks, sports drinks, alcoholic beverages, tea, etc.

The food product of the present invention may also be in the form of pharmaceutical preparations such as capsules, etc., or in the form of a processed food such as natural liquid diets, defined formula diets and elemental diets formulated with the oil and fat of the present invention together with proteins, sugars, trace elements, vitamins, emulsifiers, aroma chemicals, etc., health drinks, enteral nutrients, and the like.

As described above, lipids, especially triacylglycerols can be efficiently produced by expressing the diacylglycerol acyltransferase gene of the present invention in host cells.

In addition, the expression level of the gene can be used as an indicator to study culture conditions, cultivation control, etc. for efficient production of lipids, especially triacylglycerols.

EXAMPLES

Hereinafter, the present invention is described in more detail with reference to EXAMPLES but it should be understood that the invention is not deemed to limit the scope of the invention to these EXAMPLES.

Genome Analysis of *M. alpina*

The *M. alpina* 1S-4 strain was plated on 100 ml of GY2:1 medium (2% glucose and 1% yeast extract, pH 6.0) followed by shake culture at 28° C. for 2 days. The fungal cells were collected by filtration, and genomic DNA was prepared using DNeasy (QIAGEN).

The nucleotide sequence of the genomic DNA described above was determined using a Roche 454 Genome Sequencer FLX Standard. This case involved two runs of nucleotide sequencing of a fragment library and three runs of nucleotide sequencing of a mate paired library. The resulting nucleotide sequences were assembled into 300 supercontigs.

Search of *S. cerevisiae*-Derived LRO1 (ScLRO1) Homologs

Using as a query the putative amino acid sequence (GenBank Accession No. P40345) encoded by *S. cerevisiae*-derived PDAT gene (ScLRO1), a tblastn search was performed against the genome nucleotide sequence of the *M. alpina* strain 1S-4. As a result, a hit was found in a supercontig containing the sequence shown by SEQ ID NO: 5. The gene bearing the nucleotide sequence of SEQ ID NO: 5 was designated as MaLRO1 and cDNA was cloned as follows.

Preparation of cDNA Library

*M. alpina* strain 1S-4 was inoculated into 100 ml of medium (1.8% glucose and 1% yeast extract, pH 6.0) and pre-cultured for 3 days at 28° C. A 10 L culture vessel (Able Co., Tokyo) was charged with 5 L of medium (1.8% glucose, 1% soybean powder, 0.1% olive oil, 0.01% Adekanol, 0.3% $KH_2PO_4$, 0.1% $Na_2SO_4$, 0.05% $CaCl_2.2H_2O$ and 0.05% $MgCl_2.6H_2O$, pH 6.0), and the whole amount of the pre-cultured product was inoculated therein, followed by aerobic spinner culture under conditions of 300 rpm, 1 vvm and 26° C. for 8 days. On Days 1, 2 and 3 of the culture, glucose was added in an amount corresponding to 2%, 2% and 1.5%, respectively. The cells were collected at each stage of the culture on Day 1, 2, 3, 6 or 8 to prepare total RNA by the guanidine hydrochloride/CsCl method. Using an Oligotex-dT30<Super>mRNA Purification Kit (Takara Bio), poly(A)+ RNA was purified from the total RNA. A cDNA library was prepared for each stage with a ZAP-cDNA Gigapack III Gold Cloning Kit (STRATAGENE).

cDNA Cloning

For cloning of cDNA for MaLRO1, the following primers were prepared based on SEQ ID NO: 5.

```
                                            (SEQ ID NO: 6)
MaLRO1-1F:   5'-CCTGGAATCGTATCAACTGGCCTTG-3'

(SEQ ID NO: 7)
MaLRO1-3R:   5'-CAGGTCCGCCCGCTCCCGCCTCG-3'
```

Using the cDNA library prepared above as a template, amplification was performed by PCR for the cycles given below using primers MaLRO1-1F and MaLRO1-3R and ExTaq (Takara Bio).
[94° C., 2 mins.]×1 cycle,
[94° C., 1 min., 55° C., 1 min., 72° C., 1 min.]×30 cycles
[72° C., 10 mins.]×1 cycle The amplified DNA fragment of approximately 0.7 kb was purified and then cloned with the TOPO-TA-Cloning Kit (INVITROGEN CORP.).

The nucleotide sequence of the insert was confirmed by a DNA sequencer and the plasmid bearing the 814th to 1485th nucleotide sequence in SEQ ID NO: 4 was designated as pCR-MaLRO1-P. Next, this plasmid was used as a template to perform PCR with the primers described above. In PCR, ExTaq (Takara Bio Inc.) was used, but the attached dNTP mix was replaced by a PCR Labeling Mix (Roche Diagnostics) to prepare a digoxigenin (DIG)-labeled DNA to be amplified.

The probe above was used to screen the cDNA library.
Hybridization conditions were set as follows.
Buffer: 5×SSC, 1% SDS, 50 mM Tris-HCl (pH7.5), 50% formamide;
Temperature: 42° C. (overnight);
Wash conditions: in a solution of 0.2×SSC, 0.1% SDS (65° C.) for 20 mins, 3 times.

Detection was accomplished by using a DIG Nucleic Acid Detection Kit (Roche Diagnostics, Inc.). From the phage clones obtained by screening, plasmids were excised by in vivo excision to obtain the respective plasmid DNAs. In the plasmids obtained by screening, the plasmid with the longest insert was designated as plasmid pB-MaLRO1-P 1.

Figure 1A:
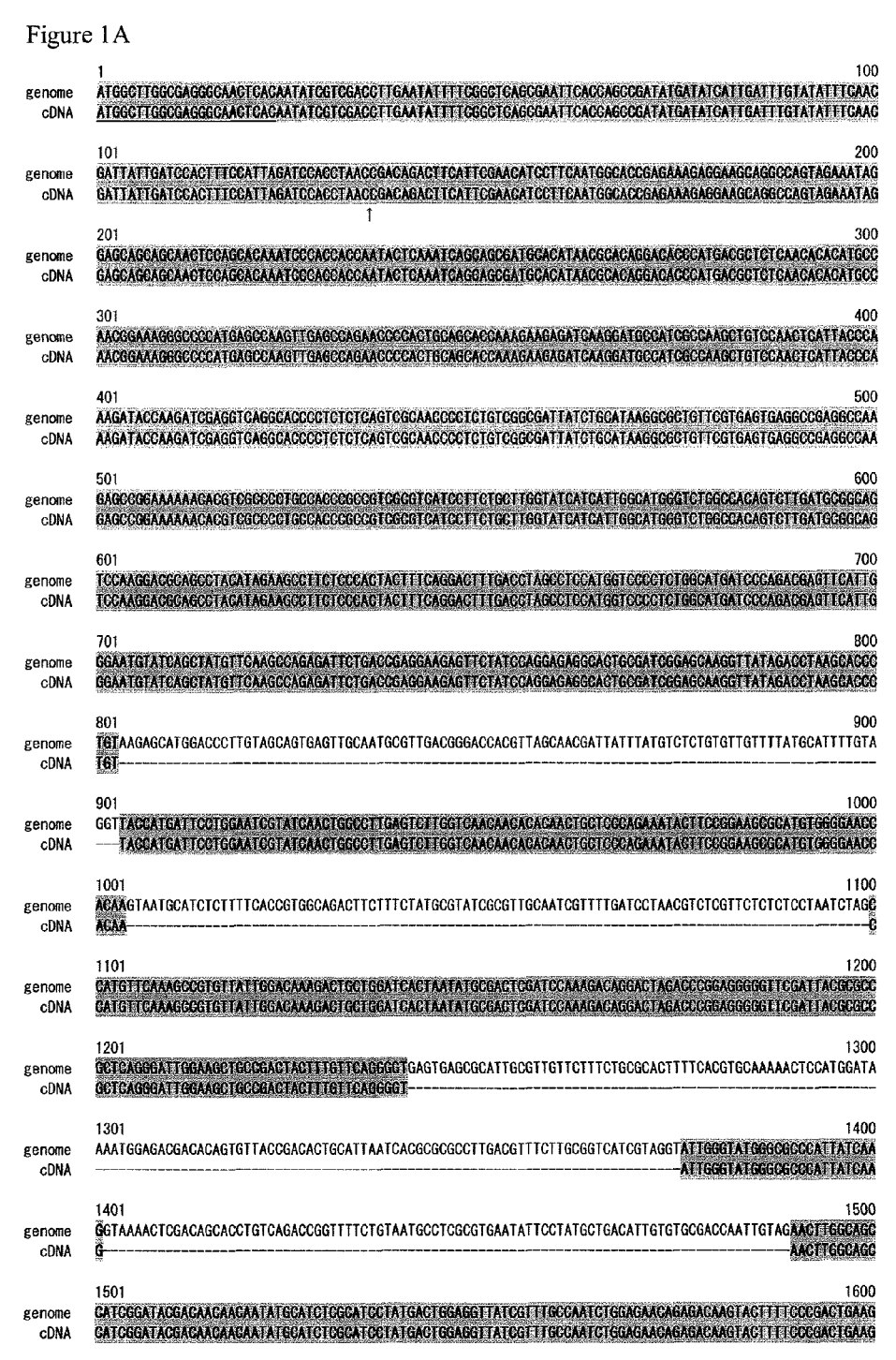

The insert sequence and the genomic sequence of plasmid pB-MaLRO1-P1 were compared. The 5' end of the insert of plasmid pB-MaLRO1-P1 is shown by the upward arrow in FIG. 1. In the genome sequence, the 5' end sequence shown by the upward arrow in the genome sequence was analyzed from the insert sequence of MaLRO1-P1 toward the upstream. Two ATGs as initiation codons were found nearer to the 3' end than the stop codon first appeared in the same frame as in the frame presumed to encode MaLRO1. Therefore, the 5' primer MaLRO1-6F containing the initiation codon at the 5' end was prepared and as the 3' primer MaLRO1-5R was also prepared.

```
                                         (SEQ ID NO: 8)
MaLRO1-5R:   5'-CTCTCCTGGATAGAACTCTTCCTCGG-3'

(SEQ ID NO: 9)
MaLRO1-6F:   5'-ATGGCTTGGCGAGGGCAACTCAC-3'
```

Using as a template the cDNA prepared from the *M. alpina* 1S-4 strain, PCR was performed using the primers MaLRO1-6F and MaLRO1-5R and ExTaq (Takara Bio). The resulting DNA fragment of approximately 0.75 kbp was cloned using the TOPO-TA Cloning Kit and the nucleotide sequence of the insert was determined. The insert contained the 1st-762nd nucleotide sequence in SEQ ID NO: 4, suggesting that the first initiation codon ATG in SEQ ID NO: 4 would be transcribed. The thus obtained nucleotide sequence was ligated to the nucleotide sequence of the insert of the plasmid pB-MaLRO1-P1 to give the nucleotide sequence of SEQ ID NO: 4; this was considered to be the nucleotide sequence of cDNA of MaLRO1.

Sequencing Analysis

The sequence of SEQ ID NO: 4 contained CDS (SEQ ID NO: 3) in the 1st-2400th nucleotide sequence and ORF (SEQ ID NO: 1) in the 1st-2397th nucleotide sequence. The amino acid sequence deduced from SEQ ID NO: 1 is shown by SEQ ID NO: 2 in FIG. 2. The genome sequence (SEQ ID NO: 5) of MaLRO1 was compared with the cDNA sequence (SEQ ID NO: 4) of MaLRO1 (FIG. 1). The results revealed that the genome sequence of MaLRO1 gene consisted of 5 introns and 6 exons.

The amino acid sequence of MaLRO1 shown by SEQ ID NO: 2 was searched against the amino acid sequence registered in GenBank using tblastp. As a result, the amino acid sequence of MaLRO1 shown by SEQ ID NO: 2 showed a certain degree of homology to the fungus-derived LRO1 homologue. The highest homology was shared with a putative protein (EAK81307) from *Ustilago maydis*, a basidiomycete, which function is unknown, indicating the identity of 35.7%. MaLRO1 shared the homology of 31.7% to LRO1 (XP_504038) from *Yarrowia lipolytica* and the homology of 28.9% to LRO1 from *S. cerevisiae*. Comparison was made between SEQ ID NO: 2 and the amino acid sequences of the fungus-derived LRO1 homologues described above (FIG. 3). The three amino acid residues considered to constitute the active center were conserved in all of the homologues.

Construction of Expression Vector

An expression vector having the structure to highly express the LRO1 gene from *M. alpina* in yeast *S. cerevisiae* was constructed.

First, primer Bam-MaLRO1-F was prepared.

```
Bam-MaLRO1-F:
                                        (SEQ ID NO: 10)
5'-GGATCCATGGCTTGGCGAGGGCAACTCAC-3'
```

Using the cDNA prepared from the *M. alpina* 1S-4 strain as a template, PCR was performed with primers Bam-MaLRO1-F and MaLRO1-5R using KOD-plus (Toyobo). The resulting DNA fragment of approximately 0.75 kbp was cloned using a Zero Blunt TOPO Cloning Kit (Invitrogen) to verify the nucleotide sequence. Comparison was made to the cDNA sequence of MaLRO1, and a plasmid having the overlapping tracts of the nucleotide sequence was designated as pCR-MaLRO1-5'. The plasmid pCR-MaLRO1-5' was digested with restriction enzymes BamHI and PstI. Using a Quick Ligation Kit (NEW ENGLAND BioLabs), the resulting DNA fragment of approximately 0.35 kbp was ligated to the DNA fragment of approximately 2.05 kbp, which was obtained by digestion of the plasmid pB-MaLRO1-P1 with restriction enzymes PstI and XhoI, and the DNA fragment of approximately 8.3 kbp, which was obtained by digestion of yeast expression vector pYE22m with restriction enzymes BamHI and SalI. The plasmid obtained was designated as pYEMaLRO1.

Expression in Yeast *S. cerevisiae* Δdga1 and Δlro1 Strains
(1) Preparation of Yeast *S. cerevisiae* Δdga1 and Δlro1 Strains
(1-1) Cloning of *S. cerevisiae*-Derived DGA1 Gene and LRO1 Gene For cloning of the full-length of *S. cerevisiae*-derived DGA1 gene (YOR245C, hereinafter referred to as ScDGA1) and LRO1 gene (YNR008W, hereinafter referred to as ScLRO1), the following primers were prepared.

```
ScDGA1-F1:
                                        (SEQ ID NO: 11)
5'-GAATTCATGTCAGGAACATTCAATGATATA-3'

ScDGA1-R1:
                                        (SEQ ID NO: 12)
5'-GTCGACTTACCCAACTATCTTCAATTCTGC-3'

ScLRO1-F1:
                                        (SEQ ID NO: 13)
5'-GAATTCATGGGCACACTGTTTCGAAGAAAT-3'

ScLRO1-R1:
                                        (SEQ ID NO: 14)
5'-GTCGACTTACATTGGGAAGGGCATCTGAGA-3'
```

One platinum loop of the yeast *S. cerevisiae* S288C strain was inoculated into 10 ml of YPD (DIFCO) liquid medium, followed by shake culture at 30° C. for a day. The cells were collected by centrifugation and DNA was extracted using GenTLE Kun (Takara Bio) for yeast.

Using this DNA as a template, PCR was performed with ExTaq (Takara Bio) using a pair of primers ScDGA1-F1 and ScDGA1-R1 or a pair of primers ScLRO1-F1 and ScLRO1-R1. The DNA fragment of approximately 1.3 kbp and the DNA fragment of approximately 2 kbp obtained from the respective pairs were cloned using a TA-Cloning Kit (Invitrogen) to confirm the nucleotide sequences. The plasmids with the correct nucleotide sequences were designated as plasmid pCR-ScDGA1 and plasmid pCR-ScLRO1, respectively.

(1-2) Construction of Plasmid pCR-Δdga1:URA3-1

The DNA fragment of approximately 4.5 kbp, which was obtained by digesting plasmid pCR-ScDGA1 with restriction enzymes HpaI and AatI, was ligated to the DNA fragment of approximately 1.2 kbp, which was obtained by digesting plasmid pURA34 (JPA 2001-120276) with restriction enzyme HindIII and then blunt ending with a DNA Blunting Kit (Takara Bio), using Ligation High (Toyobo). The plasmid, in which the URA3 gene was inserted to the same orientation as in the ScDGA1 gene, was designated as CR-Δdga1:URA3-1.

(1-3) Construction of Plasmid pUC-Δlro1:LEU2-1

The DNA fragment of approximately 2 kbp, which was obtained by digesting the plasmid pCR-ScLRO1 with restriction enzymes EcoRI and SalI, was ligated to the digestion product of pUC18 with the same restriction enzyme, using Ligation High (Toyobo) to give plasmid pUC-ScLRO1. This plasmid was digested with restriction enzymes XbaI and ApaI, followed by blunt ending with a DNA Blunting Kit (Takara Bio). The resulting DNA fragment of approximately 3.8 kbp was ligated to the DNA fragment of approximately 2.2 kbp, which was obtained by digesting the plasmid YEp13 (GenBank Accession No. U03498) with restriction enzymes SalI and XhoI and then blunt ending, using Ligation High (Toyobo). The plasmid, in which the URA3 gene was inserted to the same orientation as in the ScDGA1 gene, was designated as pUC-Δlro1:LEU2-1.

(1-4) Acquisition of Transformant

Using the *S. cerevisiae* YPH499 strain (ura3-52 lys2-801amber ade2-101ochre trp1-Δ63 his3-Δ200 leu2-Δ1 a) (STARATAGENE) as a host, transformants were prepared as follows. Specifically, co-transformation was performed by the lithium acetate method, using the DNA fragment amplified by PCR with a pair of primers ScDGA1-F1 and ScDGA1-R1 and the plasmid pCR-Δdga1:URA3-1 as a template, and the DNA fragment amplified by PCR with a pair of primers ScLRO1-F1 and ScLRO1-R1 and the plasmid pUC-Δlro1:LEU2-1 as a template. The resulting transformants were screened by the ability to grow on SC-Leu,Ura agar medium (2% agar) (per liter, 6.7 g of yeast nitrogen base w/o amino acids (DIFCO), 20 g of glucose and 1.3 g of amino acid powders (a mixture of 1.25 g of adenine sulfate, 0.6 g of arginine, 3 g of aspartic acid, 3 g of glutamic acid, 0.6 g of histidine, 0.9 g of lysine, 0.6 g of methionine, 1.5 g of phenylalanine, 11.25 g of serine, 0.9 g of tyrosine, 4.5 g of valine, 6 g of threonine and 1.2 g of tryptophan). Among the transformants thus obtained, DNAs were extracted from random two cells using GenTLE Kun (Takara Bio) for yeast. Using these DNAs as templates, PCR was performed using the following pairs of primers (1) to (4).
(1) ScDGA1-F1 and ScDGA1-R1
(2) ScDGA1-F1 and ScDGA1-R2
(3) ScLRO1-F1 and ScLRO1-R1
(4) ScLRO1-F1 and ScLRO1-R2

```
                             (SEQ ID NO: 15)
ScDGA1-R2:   5'-GACCAGTGTCATCAGAGAAATAGG-3'

(SEQ ID NO: 16)
ScLRO1-R2:   5'-GAGCTGGAACTGCCTTTGGAGC-3'
```

As a result, the DNA fragment of 1.8 kbp was amplified by the pair (1) and the DNA fragment of 3.3 kbp was amplified by the pair (3), but the DNA fragment was not amplified by the pair (2) or (4), in any of the strains. From the results it could be confirmed that these strains were the Δdga1, Δlro1 strains. Random one of these strains was used as the host for the following transformants.

(2) Transfection to Yeast *S. cerevisiae* Δdga1, Δlro1 Strains and Analysis (2-1) Acquisition of Transformants The Δdga1, Δlro1 strains as hosts were transformed into plasmids pYE22m and pYE-MaLRO1, respectively, by the lithium acetate method. The transformants were screened for the ability to grow on SC-Trp,Leu,Ura agar medium (2% agar) (per liter, 6.7 g of yeast nitrogen base w/o amino acids (DIFCO), 20 g of glucose, 1.3 g of amino acid powders (a mixture of 1.25 g of adenine sulfate, 0.6 g of arginine, 3 g of aspartic acid, 3 g of glutamic acid, 0.6 g of histidine, 0.9 g of lysine, 0.6 g of methionine, 1.5 g of phenylalanine, 11.25 g of serine, 0.9 g of tyrosine, 4.5 g of valine and 6 g of threonine). Random two strains from the respective plasmid-transfected strains were used for the following cultivation tests. That is, the strains transformed into pYE22m were designated as C/ΔDG#1, 2 and the strains transformed into pYE-MaLRO1 were designated as MaLRO1/ΔDG#1, 2.

(2-2) Cultivation of Transformants

One platinum loop each of the four transformants of C/ΔDG#1, 2 and MaLRO1/ΔDG#1, 2 was inoculated into 10 ml of SC-Trp,Leu,Ura liquid medium, followed by shake culture at 30° C. overnight. The resulting culture solution, 1 ml, was inoculated into 10 ml of YPDA liquid medium (1% yeast extract, 2% peptone, 2% glucose and 0.0075% 1-adenine hemisulfate salt), followed by shake culture at 30° C. for 24 hours. The cells were collected by centrifugation, washed with water and then lyophilized. The lyophilized cells were disrupted with glass beads and the lipids were extracted with 8 ml of chloroform:methanol=2:1. Thin layer chromatography (TLC) was performed on a Silica Gel 60 Plate (Merck) under the conditions of hexane:diethyl ether:acetic acid=70:30:1 as the developing solvent to fractionate lipids. The lipids were detected by spraying an aqueous solution of 0.015% primulin and 80% acetone (primulin solution) and irradiating with UV rays to visualize the lipids. The triacylglycerol (TG) fraction and the phospholipid (PL) fraction were marked with a pencil and the silica gels were scraped off, respectively, and transferred to test tubes. After the fatty acids were converted to the methyl esters by the hydrochloric acid methanol method, the analysis of fatty acids was performed by gas chromatography. More specifically, the fatty acids were converted to the methyl esters by adding 1 ml of dichloromethane and 2 ml of 10% hydrochloric acid-methanol and reacting them at 50° C. for 3 hours. Subsequently, 4 ml of hexane and 1 ml of water were added to the reaction mixture, which was then vigorously stirred. The mixture was then centrifuged and the upper layer was fractionated. The solvent was removed by distillation using a speed-vac and the residue was dissolved in acetonitrile. The solution was provided for gas chromatography for fatty acid analysis. In the methylation reaction described above, tricosanoic acid was added as an internal standard to quantify the fatty acid content. The results are shown in FIG. 4.

In the MaLRO1/ΔDG#1, 2 strains in which MaLRO1 as the PDAT homologue from *M. alpina* was expressed, the TG level increased by about 10 times as compared to the C/ΔDG#1, 2 strains as the control, suggesting that MaLRO1 would have the TG synthesis activity Expression in Arachidonic Acid-Producing Yeast (1) Breeding of Arachidonic Acid-Producing Yeast Strains To breed arachidonic acid-producing yeast strain (*S. cerevisiae*), the following plasmids were constructed.

First, using the cDNA prepared from *M. alpina* strain 1S-4 as a template, PCR was performed with ExTaq using the primer pair of Δ12-f and Δ12-r, Δ6-f and Δ6-r, GLELO-f and GLELO-r, or Δ5-f and Δ5-r thereby to amplify the Δ12 fatty acid desaturase gene (GenBank Accession No. AB020033), the Δ6 fatty acid desaturase gene (GenBank Accession No. AB020032), the GLELO fatty acid elongase gene (GenBank Accession No. AB 193123) and the Δ5 fatty acid desaturase gene (GenBank Accession No. AB 188307) in the *M. alpina* strain 1S-4.

```
Δ12-f:    TCTAGAATGGCACCTCCCAACACTATTG        (SEQ ID NO: 17)

Δ12-r:    AAGCTTTTACTTCTTGAAAAAGACCACGTC      (SEQ ID NO: 18)

Δ6-f:     TCTAGAATGGCTGCTGCTCCCAGTGTGAG       (SEQ ID NO: 19)

Δ6-r:     AAGCTTTTACTGTGCCTTGCCCATCTTGG       (SEQ ID NO: 20)

GLELO-f:  TCTAGAATGGAGTCGATTGCGCAATTCC        (SEQ ID NO: 21)

GLELO-r:  GAGCTCTTACTGCAACTTCCTTGCCTTCTC      (SEQ ID NO: 22)

Δ5-f:     TCTAGAATGGGTGCGGACACAGGAAAAACC      (SEQ ID NO: 23)

Δ5-r:     AAGCTTTTACTCTTCCTTGGGACGAAGACC      (SEQ ID NO: 24)
```

These genes were cloned with the TOPO-TA-Cloning Kit. The clones were confirmed for their nucleotide sequences, and the clones containing the nucleotide sequences of the Δ12 gene, Δ6 gene, GLELO gene and Δ5 gene were designated as plasmids pCR-MAΔ12DS (containing the nucleotide sequence of the Δ12 gene), pCR-MAΔ6DS (containing the nucleotide sequence of the Δ6 gene), pCR-MAGLELO (containing the nucleotide sequence of the GLELO gene) and pCR-MAΔ5DS (containing the nucleotide sequence of the Δ5 gene), respectively.

On the other hand, the plasmid pURA34 (JPA 2001-120276) was digested with restriction enzyme HindIII. The resulting DNA fragment of approximately 1.2 kb was inserted into the HindIII site of the vector, which was obtained by digesting pUC18 vector with restriction enzymes EcoRI and SphI, then blunt ending and self ligating said vector. The clone in which the EcoRI site of the vector was located at its 5' end of URA3 was designated as pUC-URA3. Also, the DNA fragment of approximately 2.2 kb, which was obtained by digesting YEp13 with restriction enzymes SalI and XhoI, was inserted into the SalI site of vector pUC18. The clone in which the EcoRI site of the vector was located at its 5' end of LUE2 was designated as pUC-LEU2.

Next, the plasmid pCR-MAΔ12DS was digested with restriction enzyme HindIII, followed by blunt ending and further digestion with restriction enzyme XbaI. The resulting DNA fragment of approximately 1.2 kbp was ligated to the DNA fragment of approximately 6.6 kbp, which was obtained by digesting vector pESC-URA (STRATAGENE) with restriction enzyme SacI, blunt ending and further digesting with restriction enzyme SpeI, thereby to give plasmid pESC-U-Δ12. The plasmid pCR-MAΔ6DS was digested with restriction enzyme XbaI, followed by blunt ending and further digestion with restriction enzyme HindIII. The resulting DNA fragment of approximately 1.6 kbp was ligated to the DNA fragment of approximately 8 kbp, which was obtained by digesting the plasmid pESC-U-Δ12 with restriction enzyme SalI, blunt ending and further digesting with restriction enzyme HindIII, thereby to give plasmid pESC-U-Δ12:Δ6. This plasmid was partially digested with restriction enzyme PvuII. The resulting fragment of approximately 4.2 kb was inserted into the SmaI site of pUC-URA3 to give plasmid pUC-URA-Δ12:Δ6.

Also, the plasmid pCR-MAGLELO was digested with restriction enzymes XbaI and SacI. The resulting DNA fragment of approximately 0.95 kbp was ligated to the DNA fragment of approximately 7.7 kbp, which was obtained by digesting vector pESC-LEU (STRATAGENE) with restriction enzymes XbaI and SacI, thereby to give plasmid pESC-L-GLELO. The plasmid pCR-MAΔ5DS was digested with restriction enzyme XbaI, followed by blunt ending and further digestion with restriction enzyme HindIII. The resulting DNA fragment of approximately 1.3 kbp was ligated to the DNA fragment of approximately 8.7 kbp, which was obtained by digesting the plasmid pESC-L-GLELO with restriction enzyme ApaI, blunt ending and further digesting with restriction enzyme HindIII, thereby to give plasmid pESC-L-GLELO:Δ5. This plasmid was digested with restriction enzyme PvuII and the resulting fragment of approximately 3.2 kbp was inserted into the SmaI site of pUC-LEU2 to give plasmid pUC-LEU-GLELO:Δ5. *Saccharomyces cerevisiae* strain YPH499 (STRATAGENE) was co-transformed into the plasmid pUC-URA-Δ12:Δ6 and the plasmid pUC-LEU-GLELO:Δ5. The transformants were screened by the ability to grow on SC-Leu,Ura agar medium. Among the transformants thus obtained, random one strain was designated as the strain ARA3-1. By culturing this strain in a galactose-supplemented medium, the strain becomes capable of expressing from the GAL1/10 promoter the Δ12 fatty acid desaturase gene, the Δ6 fatty acid desaturase gene, the GLELO gene and the Δ5 fatty acid desaturase gene.

(2) Transformation into Arachidonic Acid-Producing Yeast and Analysis

The ARA3-1 strain was transformed into plasmids pYE22m and pYE-MaLRO1. Transformants were screened by the ability to grow on SC-Trp, Leu, Ura agar medium (2% agar) (per liter, 6.7 g of yeast nitrogen base w/o amino acids (DIFCO), 20 g of glucose and 1.3 g of amino acid powders (a mixture of 1.25 g of adenine sulfate, 0.6 g of arginine, 3 g of aspartic acid, 3 g of glutamic acid, 0.6 g of histidine, 0.9 g of lysine, 0.6 g of methionine, 1.5 g of phenylalanine, 11.25 g of serine, 0.9 g of tyrosine, 4.5 g of valine and 6 g of threonine). Random four strains from the respective plasmid-transfected strains were used for the subsequent cultivation.

These strains were each cultured at 30° C. for a day in 10 ml of the SC-Trp,Leu,Ura liquid medium described above. For these strains, 1 ml of the culture was then cultured at 15° C. for 6 days in 10 ml of SG-Trp,Leu,Ura liquid medium (per liter, 6.7 g of yeast nitrogen base w/o amino acids (DIFCO), 20 g of galactose and 1.3 g of amino acid powders (a mixture of 1.25 g of adenine sulfate, 0.6 g of arginine, 3 g of aspartic acid, 3 g of glutamic acid, 0.6 g of histidine, 0.9 g of lysine, 0.6 g of methionine, 1.5 g of phenylalanine, 11.25 g of serine, 0.9 g of tyrosine, 4.5 g of valine and 6 g of threonine) added with γ-linolenic acid to become 50 μg/ml in duplicate. The cells were collected, washed with water and then lyophilized. To the lyophilized cells was added 4 ml of chloroform:methanol=2:1, which was maintained at 70° C. for an hour. Thereafter, centrifugation was performed to recover the supernatant. To the remaining cells was further added 4 ml of chloroform:methanol=2:1. The mixture was centrifuged and the resulting supernatant was recovered together with the supernatant previously recovered. The solvent was removed by distillation using a speed-vac and the residue was dissolved in a small quantity of chloroform. TLC was performed on a Silica Gel 60 Plate (Merck) under the conditions of hexane:diethyl ether:acetic acid=70:30:1 as the developing solvent to fractionate lipids. The lipids were detected by spraying the primulin solution and irradiating with UV rays. The TG fraction and the PL fraction were scraped off, respectively, and each transferred to a test tube. After the fatty acids were converted to the methyl esters by the hydrochloric acid methanol method, the analysis of fatty acids was performed by gas chromatography.

The ratios of polyunsaturated fatty acids (PUFA) in the TG fraction and the PL fraction are shown in FIG. 5, respectively. In the MaLRO1 expression strain, the ratios of DGLA in TG and arachidonic acid (ARA) were increased, when compared to the control (FIG. 5A). The yeast strains used in EXAMPLE above had been imparted with the ability to produce arachidonic acid by inserting the genes for the Δ12 fatty acid desaturase, Δ6 fatty acid desaturase, GLELO and Δ5 fatty acid desaturase, and had the arachidonic acid-producing system in a similar manner as M. alpina. In M. alpina, GLELO produces DGLA from γ-linolenic acid (GLA) bound to CoA, and DGLA is taken up into lipids. Then, Δ5 fatty acid desaturase acts on DGLA present mainly as acyl residues of phosphatidylcholine to produce ARA. It is therefore considered that as in M. alpina, DGLA would be in such a state bound to CoA or would be present in other lipids, and furthermore, would be present as acyl residues of phosphatidylcholine, also in the cells of the yeast strains used in EXAMPLE above. Also, ARA is considered to be produced mainly as acyl residues of phosphatidylcholine. It is therefore considered that the MaLRO1 gene would encode "phospholipids: diacylglycerol transferase," which substrate is a phospholipid.

On the other hand, it was noted from the fatty acid content in the phospholipids that the proportions of DGLA and ARA were the same as in the control and the MaLRO1 expression strain (FIG. 5B).

These results suggested the possibility that MaLRO1 would be highly specific to DGLA and ARA and efficiently produce TG with higher contents of DGLA and ARA by using MaLRO1.

Construction of Vector for M. alpina Expression

The vector used for the expression of M. alpina was pDuraMCS, which allowed the expression of a target gene from the histone promoter.

To express the MaLRO1 gene in M. alpina, a vector was constructed as follows. The plasmid pCR-MaLRO1-5' was digested with restriction enzymes BamHI and PstI. The resulting DNA fragment of approximately 0.35 kbp was ligated to the DNA fragment of approximately 2.05 kbp, which was obtained by digesting plasmid pB-MaLRO1-P1 with restriction enzymes PstI and XhoI, and the DNA fragment of approximately 8.3 kbp, which was obtained by digesting the vector pDuraMCS for M. alpina expression with restriction enzymes BamHI and SalI, using a Quick Ligation Kit (NEW ENGLAND BioLabs). The plasmid obtained was designated as pDuraMCS-MaLRO1.

Acquisition of M. alpina Transformants

Using the uracil-auxotrophic strain Aura-3 derived from M. alpina strain 1S-4 as described in PCT International Publication Pamphlet WO 2005019437 entitled "Method of Breeding Lipid-Producing Fungus") as a host, transformation was performed with this plasmid by the particle delivery method. For screening of the transformants, SC agar medium was used (0.5% Yeast Nitrogen Base w/o Amino Acids and Ammonium Sulfate (Difco), 0.17% ammonium sulfate, 2% glucose, 0.002% adenine, 0.003% tyrosine, 0.0001% methionine, 0.0002% arginine, 0.0002% histidine, 0.0004% lysine, 0.0004% tryptophan, 0.0005% threonine, 0.0006% isoleucine, 0.0006% leucine, 0.0006% phenylalanine, and 2% agar).

Evaluation of M. alpina Transformants

The 13 transformants obtained were inoculated into 10 ml of GY medium (2% glucose and 1% yeast extract) and cultured at 28° C. and 300 rpm for 10 days. The transformant with higher arachidonic acid production was screened and designated as the strain LRO1-1.

The resulting 13 transformants were each inoculated into 4 ml GY medium and cultured with shaking at 28° C. for 2 days. The cells were collected by filtration, and RNA was extracted with an RNeasy Plant Kit (QIAGEN). A SuperScript First Strand System for RT-PCR (Invitrogen) was used to synthesize cDNA. To confirm expression of the MaLRO1 gene from the introduced construct, RT-PCR was performed with the following primer pairs:

```
Primer PD4P:
                                      (SEQ ID NO: 25)
5'-CGCATCCCGCAAACACACAC-3'

Primer MaLRO1-5R:
                                      (SEQ ID NO: 8)
5'-CTCTCCTGGATAGAACTCTTCCTCGG-3'
```

To confirm expression of the MaLRO1 gene including the endogenous MaLRO1 gene and the MaLRO1 gene in the construct introduced, PCR was performed using a pair of the primers MaLRO1-1F and MaLRO1-3R and a pair of the primers MaLRO1-2F and MaLRO1-4R below. The DNA fragments amplified were confirmed by agarose gel electrophoresis. When the PCR cycle was set at 20 cycles, the band corresponding to the DNA fragment amplified by the LRO1-1 strain was obviously denser than the control strain. From the results it was confirmed that the expression level of the MaLRO1 gene was increased in the LRO1-1 strain, when compared to the control strain.

```
                                      (SEQ ID NO: 6)
MaLRO1-1F:   5'-CCTGGAATCGTATCAACTGGCCTTG-3'

(SEQ ID NO: 7)
MaLRO1-3R:   5'-CAGGTCCGCCCGCTCCCGCCTCG-3'

(SEQ ID NO: 26)
MaLRO1-2F:   5'-GGCGGACCCAACTGGGTGAACGAC-3'

(SEQ ID NO: 27)
MaLRO1-4R:   5'-TCACAAGTCGACCTTGGCAGAGTAC-3'
```

Fatty Acid Analysis

The transformant LRO1-1 and the M. alpina strain 1S-4 (control) were inoculated (n=3) into 4 ml of GY medium and shake cultured at 28° C. and 125 rpm. On Day 9 of the cultivation, the total amount of the cells were recovered by filtration and lyophilized. After a portion (about 10-20 mg) of the lyophilized cells was fractionated, the fatty acids in the cells were converted into the methyl esters by the hydrochloric acid-methanol method and extracted with hexane. The residue obtained by removal of hexane with distillation was analyzed for the ratio of arachidonic acid ("ARA (%)" in TABLE 1) in the total fatty acids in the cells, using gas chromatography.

TABLE 1

Ratio of Arachidonic Acid in Total Fatty Acids in Cells

|  | LRO1-1 | Control |
|---|---|---|
| ARA (%) | 56.77 ± 0.90 | 52.42 ± 2.99 |

Mean ± SD

As shown in TABLE 1, high expression of the MaLRO1 gene in M. alpina allowed an increase in the ratio of arachidonic acid in the total fatty acids.

To a portion (about 10-20 mg) of the lyophilized cells was added 4 ml of chloroform:methanol=2:1. The mixture was maintained at 70° C. for an hour and centrifuged to recover the supernatant. To the remaining cells was further added 4 ml of chloroform:methanol=2:1. The mixture was then centrifuged to recover the supernatant. The supernatant was recovered together with the supernatant previously recovered. The solvent was removed by distillation using a speed-vac and the residue was dissolved in a small quantity of chloroform. TLC was performed on a Silica Gel 60 Plate (Merck) under the conditions of hexane:diethyl ether:acetic acid=70:30:1 as the developing solvent to fractionate lipids. The lipids were detected by spraying the primulin solution and irradiating with UV rays.

The triglyceride (TG) fraction was scraped off and transferred to a test tube. After the fatty acids were converted to the methyl esters by the hydrochloric acid methanol method, the analysis of fatty acids was performed by gas chromatography.

TABLE 2

| Ratio of Arachidonic Acid in Total Fatty Acids in TG | | |
|---|---|---|
| | LRO1-1 | Control |
| ARA (%) | 58.82 ± 1.32 | 55.00 ± 3.42 |

Mean ± SD

As shown in TABLE 2, high expression of the MaLRO1 gene in *M. alpina* allowed an increase in the ratio of arachidonic acid in the triglycerides.

INDUSTRIAL APPLICABILITY

By expressing the polynucleotide of the present invention in a suitable host cell, triacylglycerols with the high content of DGLA or ARA can be produced efficiently. The fatty acids produced in host cells by the present invention can be used to manufacture food products, cosmetics, pharmaceuticals, soaps, etc.

SEQUENCE LISTING FREE TEXT

SEQ ID NO: 6: synthetic DNA
SEQ ID NO: 7: synthetic DNA
SEQ ID NO: 8: synthetic DNA
SEQ ID NO: 9: synthetic DNA
SEQ ID NO: 10: synthetic DNA
SEQ ID NO: 11: synthetic DNA
SEQ ID NO: 12: synthetic DNA
SEQ ID NO: 13: synthetic DNA
SEQ ID NO: 14: synthetic DNA
SEQ ID NO: 15: synthetic DNA
SEQ ID NO: 16: synthetic DNA
SEQ ID NO: 17: synthetic DNA
SEQ ID NO: 18: synthetic DNA
SEQ ID NO: 19: synthetic DNA
SEQ ID NO: 20: synthetic DNA
SEQ ID NO: 21: synthetic DNA
SEQ ID NO: 22: synthetic DNA
SEQ ID NO: 23: synthetic DNA
SEQ ID NO: 24: synthetic DNA
SEQ ID NO: 25: synthetic DNA
SEQ ID NO: 24: synthetic DNA
SEQ ID NO: 25: synthetic DNA

The invention claimed is:

1. A non-naturally occurring polynucleotide according to any one selected from the group consisting of (a) to (c) below:
   (a) a polynucleotide comprising the nucleotide sequence of SEQ ID NO: 1 or 4;
   (b) a polynucleotide encoding a protein consisting of the amino acid sequence of SEQ ID NO: 2; and
   (c) a polynucleotide encoding a protein having an amino acid sequence having at least 90% sequence identity to the amino acid sequence of SEQ ID NO: 2, and having a diacylglycerol acyltransferase activity.

2. The polynucleotide according to claim 1, comprising the nucleotide sequence of SEQ ID NO: 1 or 4.

3. The polynucleotide according to claim 1, encoding a protein consisting of the amino acid sequence of SEQ ID NO: 2.

4. The polynucleotide according to claim 1, which is a DNA.

5. A protein encoded by the polynucleotide according to claim 1.

6. A vector comprising the polynucleotide according to claim 1.

7. A non-human microorganism transformed with the polynucleotide according to claim 1.

8. A non-human microorganism transformed with the vector according to claim 6.

9. The transformant according to claim 7, wherein the transformant is a lipid-producing fungus.

10. The transformant according to claim 9, wherein the lipid-producing fungus is *Mortierella alpina*.

11. A method for producing a lipid or fatty acid composition, which comprises collecting the lipid or fatty acid composition from the culture of the transformant according to claim 7.

12. The method according to claim 11, wherein the lipid is a triacylglycerol.

13. The method according to claim 11, wherein the fatty acid is arachidonic acid or dihomo-γ-linolenic acid.

* * * * *